(12) United States Patent
Li et al.

(10) Patent No.: US 8,859,288 B2
(45) Date of Patent: Oct. 14, 2014

(54) PH-SENSITIVE MICROPARTICLES WITH MATRIX-DISPERSED ACTIVE AGENT

(75) Inventors: Wenyan Li, Orlando, FL (US); Jerry W. Buhrow, Viera, FL (US); Scott T. Jolley, Titusville, FL (US); Luz M. Calle, Merritt Island, FL (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 280 days.

(21) Appl. No.: 13/542,155

(22) Filed: Jul. 5, 2012

(65) Prior Publication Data

US 2013/0017612 A1 Jan. 17, 2013

Related U.S. Application Data

(60) Provisional application No. 61/506,295, filed on Jul. 11, 2011.

(51) Int. Cl.
| | |
|---|---|
| *G01N 31/22* | (2006.01) |
| *G01N 21/81* | (2006.01) |
| *G01N 33/20* | (2006.01) |
| *B01J 13/18* | (2006.01) |
| *B01J 13/14* | (2006.01) |
| *B32B 27/42* | (2006.01) |
| *A61K 9/58* | (2006.01) |
| *A61K 9/52* | (2006.01) |
| *A61K 9/50* | (2006.01) |
| *C09D 5/08* | (2006.01) |
| *G01N 21/00* | (2006.01) |
| *G01N 21/80* | (2006.01) |
| *C09D 7/12* | (2006.01) |
| *G01N 21/64* | (2006.01) |
| *C08K 9/10* | (2006.01) |

(52) U.S. Cl.
CPC ............... *G01N 21/00* (2013.01); *C09D 5/082* (2013.01); *G01N 2021/6439* (2013.01); *G01N 21/80* (2013.01); *C08K 9/10* (2013.01); *C09D 7/1291* (2013.01); *C09D 5/08* (2013.01); *G01N 21/643* (2013.01)
USPC .......... 436/6; 106/241; 264/4.1; 264/4.7; 422/82.05; 422/82.08; 422/82.09; 422/400; 422/425; 424/490; 424/497; 427/213.3; 427/213.34; 427/213.36; 428/402.21; 428/402.24; 436/163; 503/214; 503/215; 523/205; 523/207; 523/208; 523/210

(58) Field of Classification Search
USPC ............ 106/241; 264/4.1, 4.7; 422/400, 425, 422/82.05, 82.08–82.09; 424/490, 497; 427/213.3, 213.34, 213.36; 428/402.21, 402.24; 436/6, 163; 503/214–215; 523/205, 207–208, 210
See application file for complete search history.

(56) References Cited

U.S. PATENT DOCUMENTS 3,926,830 A * 12/1975 Horiguchi et al. ............ 510/100
4,233,178 A * 11/1980 Fuchigami ............... 428/402.21
(Continued)

OTHER PUBLICATIONS

Yuan, Y. C. et al, Polymer 2008, 49, 2531-2541.*
(Continued)

*Primary Examiner* — Arlen Soderquist
(74) *Attorney, Agent, or Firm* — Michelle L. Ford; Hugh McTavish

(57) ABSTRACT

Methods to produce pH-sensitive microparticles that have an active agent dispersed in a polymer matrix have certain advantages over microcapsules with an active agent encapsulated in an interior compartment/core inside of a polymer wall. The current invention relates to pH-sensitive microparticles that have a corrosion-detecting or corrosion-inhibiting active agent or active agents dispersed within a polymer matrix of the microparticles. The pH-sensitive microparticles can be used in various coating compositions on metal objects for corrosion detecting and/or inhibiting.

35 Claims, 22 Drawing Sheets

(56) References Cited

U.S. PATENT DOCUMENTS

| | | | |
|---|---|---|---|
| 4,273,671 A * | 6/1981 | Allinikov | 252/301.19 |
| 4,318,709 A * | 3/1982 | Falb et al. | 436/163 |
| 4,568,518 A * | 2/1986 | Wolfbeis et al. | 422/420 |
| 4,632,119 A * | 12/1986 | Reichstein | 600/350 |
| 4,743,507 A | 5/1988 | Franses et al. | |
| 6,022,501 A * | 2/2000 | Dexter et al. | 264/4.7 |
| 6,075,072 A * | 6/2000 | Guilbert et al. | 523/200 |
| 6,544,540 B2 | 4/2003 | Van Koppenhagen et al. | |
| 7,670,845 B2 * | 3/2010 | Wenzel et al. | 436/163 |
| 7,790,225 B1 | 9/2010 | Calle et al. | |
| 2002/0004059 A1 * | 1/2002 | Van Koppenhagen et al. | 424/408 |
| 2002/0081431 A1 * | 6/2002 | Schmdt | 428/402 |
| 2003/0068824 A1 | 4/2003 | Frankel et al. | |
| 2004/0178986 A1 * | 9/2004 | Kokeguchi | 345/107 |
| 2004/0191653 A1 * | 9/2004 | Kokeguchi | 430/39 |
| 2006/0128569 A1 * | 6/2006 | Bell | 504/359 |
| 2007/0011951 A1 | 1/2007 | Gaeta et al. | |
| 2007/0196410 A1 * | 8/2007 | Jadhav et al. | 424/408 |
| 2008/0306026 A1 * | 12/2008 | Shirley et al. | 514/89 |
| 2008/0306584 A1 | 12/2008 | Kramer-Brown | |
| 2009/0181466 A1 * | 7/2009 | Wenzel et al. | 436/163 |
| 2010/0242788 A1 | 9/2010 | Calle et al. | |

OTHER PUBLICATIONS

Grigoriev, D. 0. et al, Soft Matter 2009, 5, 1426-1432.*

Irfan, M. et al, Inductrial Chemistry and Engineering Research 2010, 49, 1169-1196.*

V. Balamuralidhara, et al. 2011. "pH Sensitive Drug Delivery Systems: A Review." American Journal of Drug Discovery and Development 1 (1):24-48.

L.M. Calle, et al 2010. "A Multifunctional Coating for Autonomous Corrosion Control." 42nd International SAMPE Technical Conference. Salt Lake City, UT. Oct. 11-14, 2010.

P. Dahlsten, et al. 2009. "Electrokinetic bahavior of melamine-formaldehyde latex particles at moderate electrolyte concentration." Journal of Colloid and Interface Science 339:409-415.

B. Friedel, et al. 2006. "Preparation of Monodisperse, Submicrometer Carbon Spheres by Pyrolysis of Melamine—Formaldehyde Resin." Small 2 (7):859-863.

I.W. Cheong, et al. 2004. "Preparation of Monodisperse Melamine-Formaldehyde Microspheres via Dispersed Polycondensation." Macromolecular Research 12 (2):225-232.

S.A. Vitale, et al. 2003. "Liquid Droplet Dispersions Formed by Homogeneous Liquid-Liquid Nucleation: "The Ouzo Effect"." Langmuir 19 (10):4105-4110.

S.R. White et al. 2001. "Autonomic healing of polymer composites." Nature 409:794-797.

P. Wojtaszczyk, et al. 1993. "Statistical Properties of Surfaces Covered by large spheres." Journal of Chemical Physics 99 (9):7198-7208.

Polydimethylsiloxane Networks: Silanol-terminated Polydimethylsiloxanes. Dow Corning. 2004. Retrieved from the Internet. <URL: http://www.dowcorning.com/content/publishedlit/26/1292-01.pdf>. p. 1. entire document.

Closed Loop Inhibitors. Guardian Chemical Specialties Corp. Aug. 17, 2003. Retrieved from the Internet. <URL: http://www.guardiancsc.com/pdf/closed.pdf>. p. 4. entire document.

* cited by examiner

A

B

A

B

A  20μm

B  20μm

A

B

C

D

A

B

A
200μm

B
200μm

A

B

C

D

E  20μm

F  20μm

G  20μm

H  20μm

I

J

K

L

A

B

A

B

C

D

E

F

PH-SENSITIVE MICROPARTICLES WITH MATRIX-DISPERSED ACTIVE AGENT

CROSS-REFERENCE TO RELATED APPLICATIONS

This application claims the benefit under 35 U.S.C. §119 (e) of U.S. Provisional Application Ser. No. 61/506,295, filed on Jul. 11, 2011, the contents of which are incorporated herein by reference.

STATEMENT OF GOVERNMENT INTEREST

The invention described herein was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or therefore. In accordance with 35 U.S.C. §202, the contractor elected not to retain title.

FIELD OF THE INVENTION

The present invention relates generally to microparticles and their formation. More particularly, this invention is related to pH-sensitive microparticles that have an active agent dispersed in a polymer matrix of the microparticles.

BACKGROUND OF THE INVENTION

Microcapsules have been used for various applications. Recently, microcapsules have been used for smart coatings for corrosion applications. For instance, the pH-sensitive microcapsules disclosed by Li and Calle in 2009 NACE International conference paper 09499, 2007 NACE International conference paper 07228, and in U.S. Pat. No. 7,790,225 B1 (Luz Calle et al., issued Sep. 7, 2010) have been used for the controlled release of a corrosion indicator, or a corrosion inhibitor, or a self-healing agent when corrosion occurs. Mechanically breakable microcapsules are also used in self-healing composites disclosed by White, et al. in Nature, 2001, 409:794-797.

Existing microcapsules are typically formed from an oil-in-water or water-in-oil emulsion and have a wall encapsulating an interior core with an active agent. The active agent is released when the microcapsule wall breaks down mechanically or chemically.

SUMMARY OF THE INVENTION

The inventors have discovered methods to produce pH-sensitive microparticles that have an active agent dispersed in a polymer matrix, instead of encapsulated in an interior compartment inside of a polymer wall, where the interior compartment substantially lacks polymer and the wall substantially lacks an active agent. The inventors have discovered that the microparticles with an active agent dispersed in the polymer matrix, as opposed to encapsulated in a polymer wall, have certain advantages. First, a much higher loading of active agent was achieved with this type of microparticle as compared to a conventional microcapsule with a wall/interior core architecture. Second, the matrix-dispersed microparticle architecture releases the active agent in a controlled but possibly incremental fashion, as some but not all of the polymer strands hydrolyze. In contrast, the microcapsules with a wall/interior core architecture release their active agent in an all-or-none manner after the capsule wall is broken. No active agent is released until the wall breaks or is penetrated, and then the entire interior core content is released or is available to the exterior milieu. It is advantageous, for corrosion inhibition in particular, for the release of the corrosion inhibitor to be proportional to the extent of corrosion because the encapsulated inhibitor reservoirs can be released in response to multiple isolated corrosion events, rather than in an all-or-none manner.

The polymer of the polymer matrix preferably has a polymer backbone or a cross-linking segment that is susceptible to hydrolysis, especially under an alkaline pH condition. This is particularly important because the particles are developed for use in coatings for corrosion detection or corrosion inhibition. The onset of corrosion often causes localized pH changes, in particular basic pH, and by having the polymer matrix susceptible to hydrolysis under these conditions, the polymer will degrade as corrosion begins to occur. As a result, the active agent is released in proportion to the extent of corrosion and in proportion to the need for the active agent.

One embodiment of the invention provides a method of forming microparticles comprising: (a) forming a water-soluble prepolymer in solution or dispersion in water-miscible solvent A from a mixture of reactants; (b) mixing an active agent or active agents dispersed or dissolved in a water-miscible solvent B with the water-soluble prepolymer in solution or dispersion in water-miscible solvent A; and (c) polycondensing the prepolymer to form a polymer matrix and to form microparticles comprising the active agent or active agents dispersed in the polymer matrix; wherein the polymer backbone or a cross-linking segment of the polymer matrix is susceptible to hydrolysis in base; wherein solvents A and B are different solvents.

In a preferred embodiment, the active agent or active agents are one or more corrosion indicators or corrosion inhibitors.

Another embodiment provides a composition comprising microparticles, the microparticles comprising: a polymer matrix and an active agent or active agents dispersed in the polymer matrix; wherein the active agent or active agents are one or more corrosion indicators or corrosion inhibitors; wherein the polymer backbone or a cross-linking segment of the polymer matrix is susceptible to hydrolysis in base.

Another embodiment provides a method of detecting corrosion comprising: (a) obtaining a metal object partially or fully coated with a coating composition comprising microparticles, the microparticles comprising: a polymer matrix and an active agent or active agents dispersed in the polymer matrix; wherein the active agent or active agents are one or more corrosion indicators; wherein the polymer backbone or a cross-linking segment of the polymer matrix is susceptible to hydrolysis in base; and (b) monitoring the object for visible changes of color or fluorescence from the one or more corrosion indicators that would indicate corrosion.

Another embodiment provides a method of producing a corrosion-resistant or corrosion-detecting metal object comprising: coating a metal object with a coating composition comprising microparticles, the microparticles comprising: a polymer matrix and an active agent or active agents dispersed in the polymer matrix; wherein the active agent or active agents are one or more corrosion indicators or corrosion inhibitors; wherein the polymer backbone or a cross-linking segment of the polymer matrix is susceptible to hydrolysis in base.

Another embodiment provides a method of forming microparticles comprising: (a) forming a water-soluble prepolymer in solution or dispersion in a water-miscible solvent A from a mixture of reactants; (b) mixing an active agent or active agents dispersed or dissolved in a water-miscible solvent B with the water-soluble prepolymer in solution or dispersion in water-miscible solvent A; and (c) polycondensing the prepolymer to form a polymer matrix and to form microparticles comprising the active agent or active agents dispersed in the polymer matrix; wherein the polymer backbone or a cross-linking segment of the polymer matrix is susceptible to hydrolysis in base; wherein solvents A and B are different solvents; and wherein the prepolymer reactants comprise a compound with at least three arms that contain ester, thioester, or anhydride bonds.

Another embodiment provides a composition comprising microparticles, the microparticles comprising: a polymer matrix and an active agent or active agents dispersed in the polymer matrix; wherein the polymer backbone or a cross-linking segment of the polymer matrix is susceptible to hydrolysis in base; wherein the polymer backbone or a cross-linking segment of the polymer matrix comprises residues of a compound having at least three arms that contain ester, thioester, or anhydride bonds.

DETAILED DESCRIPTION OF THE INVENTION

Figure 1A:
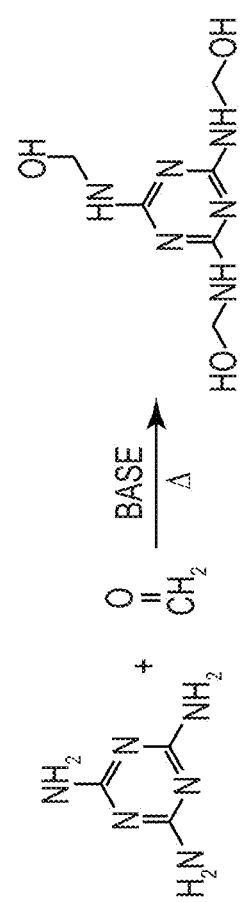
FIGS. 1A-1C show potential reactions for water-soluble Melamine (M), Formaldehyde (F), Pentaerythritol Tetra (3-Mercaptopropionate) (PTT) (MFPTT) prepolymer formation.

One embodiment of the invention provides a method of forming microparticles comprising: (a) forming a water-soluble prepolymer in solution or dispersion in water-miscible solvent A from a mixture of reactants; (b) mixing an active agent or active agents dispersed or dissolved in a water-miscible solvent B with the water-soluble prepolymer in solution or dispersion in water-miscible solvent A; (c) polycondensing the prepolymer to form a polymer matrix and to form microparticles comprising the active agent or active agents dispersed in the polymer matrix; wherein the polymer backbone or a cross-linking segment of the polymer matrix is susceptible to hydrolysis in base; wherein solvents A and B are different solvents.

Step (a) typically involves forming a water-soluble prepolymer in solution in water-miscible solvent A from a mixture of reactants. As the prepolymer becomes larger, the prepolymer may go into a dispersion, as well as or instead of a solution, in solvent A. As is discussed below, surfactant may assist in keeping the prepolymer in solution or dispersion.

Thus, in one embodiment, step (a) involves forming a water-soluble prepolymer in solution in water-miscible solvent A from a mixture of reactants.

In another embodiment, solvent A is a non-water miscible solvent or a mixture of non-water miscible solvents, whereas solvent B is a better solvent for the prepolymer than solvent A. When the active ingredient in solvent B is add to prepolymer mixture in solvent A, prepolymer concentration increases around the active ingredient in solvent B, and further polymerizes to form particles containing the active ingredient.

Preferably the active agent or active agents are one or more corrosion indicators or corrosion inhibitors. The corrosion indicators can be color or fluorescence indicators, which indicate corrosion through color change or change of their fluorescent properties. The corrosion indicators can be chosen to detect pH or ion concentration changes as a result of the corrosion process.

In some embodiments, solvents A and B are the same solvents and, in other embodiments, solvents A and B are different solvents.

Another preferred embodiment of the invention provides a method of forming microparticles comprising: (a) dissolving or dispersing the prepolymer in solvent A; and (b) dissolving or dispersing the active agent in solvent B; wherein the prepolymer in (a) will polymerize with time, with or without heating, in the presence or absence of a catalyst. When a catalyst is present, said catalyst is either an inorganic acid or an organic acid. The result of this polymerization is the formation of pH-sensitive microparticles. An active agent or active agents are introduced in solvent B during the microparticle formation process through the polymerization of the prepolymer in solvent A, as a result, microparticles containing the active agent(s) are formed.

Solvents A and B should be miscible to each other; they can be water miscible or non-water miscible solvents, or solvent mixtures.

In one embodiment, both solvents A and B can be water, when the active agent is water soluble or dispersible.

In a preferred embodiment, the active agent is water soluble and acidic, and both solvents A and B are water. When the active agent in B is added to the prepolymer mixture in solvent A, the acidic active agent causes the polymerization reaction to occur around said active agent and the active agent becomes incorporated into the particle formed during the process.

In another embodiment, both solvents A and B are water, wherein each solvent is at a different temperature. Solvent B is at a temperature wherein the active agent has a higher solubility than the temperature of solvent A. When the active agent in B is added to the prepolymer mixture in solvent A, some of the active ingredient precipitates out of the solution and is incorporated into the particles during their formation.

In another embodiment, solvent A is water or a mixture of water miscible solvents, solvent B is a water miscible solvent, or a mixture of water miscible solvents, whereas solvent B is a better solvent for the active ingredient than solvent A. When the active agent in B is added to prepolymer mixture in solvent A, some of the active agent becomes insoluble and is incorporated into the particles during their formation.

In another embodiment, solvent A is water or a mixture of water miscible solvents, solvent B is a water miscible solvent, or a mixture of water miscible solvents, whereas solvent B is a better solvent for the prepolymer than solvent A. When the active agent in solvent B is add to prepolymer mixture in solvent A, prepolymer concentration increases around the active agent in solvent B, and further polymerizes to form particles containing the active agent.

In another embodiment, solvent A is a non-water miscible solvent or a mixture of non-water miscible solvents, solvent B is a non-water miscible solvent or a mixture of non-water miscible solvents, whereas solvent B is a better solvent for the active agent than solvent A. When the active agent in B is added to prepolymer mixture in solvent A, some of the active agent becomes insoluble and is incorporated into the particles during their formation.

Likewise, another embodiment provides a composition comprising microparticles, the microparticles comprising: a polymer matrix and an active agent or active agents dispersed in the polymer matrix; wherein the polymer backbone or a cross-linking segment of the polymer matrix is susceptible to hydrolysis in base.

In one embodiment, at least 10% by weight of the microparticles is the active agent or active agents. In other embodiments, at least 15%, at least 20%, or at least 25% by weight of the microparticles is active agent.

In specific embodiments, 10-40%, 10-35%, or 10-30% by weight of the microparticles is active agent. In other embodiments, 15-40%, 15-35%, 15-30%, 20-40%, 20-35%, or 20-30% by weight of the microparticles is active agent.

In a preferred embodiment, Solvent A, in which the prepolymer is formed, is water. But it may be other water-miscible solvents. When Solvents A and B are different water-miscible solvents, the mixing of the different solvents forms, at least temporarily, an emulsion by the Ouzo effect, and the formation of this emulsion plays a significant role in the encapsulation of the active agents in the microparticles. It is also preferable, but not necessary, that the active agents have higher solubility in Solvent B than in Solvent A.

In most cases, one of solvents A and B will be water. Typically, solvent A is water and solvent B is a different water-miscible solvent. But solvents A and B could both be water-miscible solvents other than water. Or both solvents A and B could be non-water miscible solvents.

Solvent B, in specific embodiments, is ethanol, isopropanol, tetrahydrofuran (THF), N-methylpyrrolidone (NMP), dimethylformamide (DMF), 2-amino-2-methyl-1-propanol (AMP), or dimethyl sulfoxide (DMSO). In particular embodiments, solvent B is a protic solvent; in other embodiments it is an aprotic solvent. In specific embodiments, it is selected from the group consisting of NMP, DMF, and AMP.

In one embodiment, the method of forming microparticles further includes the steps of washing or separating the microparticles from the prepolymer to obtain microparticles substantially free of prepolymer and drying the microparticles substantially free of prepolymer to obtain dried microparticles. These steps were added because it was found in Example 3 that they were beneficial for forming small and monodispersed microparticles in free-flowing dry powder. Without the washing or separating steps, it appears the prepolymer continues to polymerize with groups on the particle surface to form larger particles and agglomerated particles. In one case, the separating step is performed by simply settling the microparticles, as in Example 3. The washing step also cleans the microparticle surface to eliminate excess surfactants and other surface contaminants.

In preferred embodiments, the polymer backbone of the polymer matrix is susceptible to hydrolysis in acid or base. In the Examples below, the hydrolysable group is an ester linkage. In other embodiments, it may be a thioester, anhydride, or amide linkage. In other embodiments, the linkage is an orthoester linkage. Thus, the polymer may be a polyester, polythioester, polyanhydride, polyamide, or poly(ortho ester) in particular embodiments. A polyanhydride is shown below.

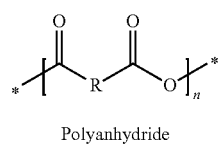

Polyanhydride

Poly(ortho esters) are prepared by the addition of diols to a diketene acetal (Scheme 1).

Scheme 1

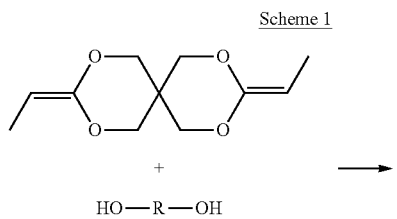

-continued

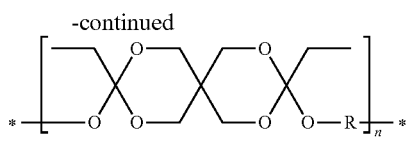

In a particular embodiment, the prepolymer reactants comprise melamine and formaldehyde. These form methylolmelamine. In the examples below, this is further reacted with pentaerythritol tetra(3-mercaptopropionate) (PTT) to form the prepolymer.

In other embodiments, the prepolymer reactants comprise urea and formaldehyde.

In specific embodiments, the prepolymer reactants comprise urea, melamine, or formaldehyde.

In some embodiments, the prepolymer reactants comprise PTT.

PTT has four mercapto groups that react with methylolmelamine (FIG. 1). Other reactants with a plurality of mercapto groups (preferably three or four mercapto groups) also have the capability of reacting in a very similar way. Thus, in some embodiments, the prepolymer reactants comprise a compound with a plurality of mercapto groups. In some embodiments, the prepolymer reactants comprise a compound with three or more mercapto groups. An example is PTT, with four mercapto groups.

In other preferred embodiments, another reactant that contains one or more ester groups and/or mercapto groups can be used instead of PTT. This reactant is selected from the group consisting of pentaerythritol tetrakis(2-mercaptoacetate), pentaerythritol, dipentaerythritol, dipentaerythritol pentaacrylate tetra(mercaptoacetate), and pentaerythritol tetraacrylate.

In other preferred embodiments, the prepolymer reactants are selected from the group consisting of melamine, urea, formaldehyde solution, low molecular weight urea formaldehyde prepolymer, melamine formaldehyde resin, polyurethane prepolymers, polyols, and low molecular weight prepolymer, such as poly(methyl methacrylate) or their monomers.

Generally, any polymer containing chemical functional groups that are susceptible for degradation under basic pH condition can be used as the polymer matrix for the pH-sensitive particles. Examples of such groups include esters, anhydrides, orthoesters, and amides. So any monomer or low molecular weight prepolymer containing these groups can potentially be used as prepolymer or cross-linking agents to form a polymer matrix that would break down through hydrolysis reaction, in which both acid and base can serve as catalysts.

For practical purposes, the amount of pH-sensitive groups and their location in the stereo-structure of the polymer are also very important. On one hand, the amount of the pH-sensitive groups should be sufficient; on the other hand, fewer pH-sensitive groups strategically located might provide high pH sensitivity in the overall polymer matrix. For example, when PTT is used as a cross-linking agent, it can form up to four bonds with neighboring polymer segments (e.g., like knotting points), and when these PTT segments are attacked they are released from the polymer matrix, thus the whole structure breaks down quickly.

It appears that the rapid decomposition that we have observed of the microparticles may be due to the fact that PTT forms part of the polymer backbone, and this has four arms radiating from a central carbon atom, where the arms contain ester groups. The polymer structure formed from a reactant with three or more arms having hydrolyzable groups is highly cross-linked, and it breaks down rapidly when even one of the arms is hydrolyzed. Furthermore, it is likely that multiple arms are hydrolyzed simultaneously if all the arms have identical hydrolyzable linkages.

Thus, in some embodiments, the prepolymer reactants comprise a compound with a plurality of ester, thioester, anhydride, orthoester, or amide bonds.

In some embodiments, the prepolymer reactants comprise a compound with at least three arms that contain ester, thioester, anhydride, amide, or orthoester bonds. More specifically, the compound contains three or more arms radiating from a central atom or central backbone, and the arms each contain ester, thioester, anhydride, amide, or orthoester bonds. PTT (FIG. 1) is an example of such a compound.

In specific embodiments, the prepolymer reactants comprise a compound with at least three arms that contain ester, thioester, or anhydride bonds.

In some embodiments, the prepolymer reactants comprise a compound with a plurality of mercapto groups. In some embodiments the prepolymer reactants comprise a compound with three or more mercapto groups, such as PTT.

In some of the examples below, the prepolymer is formed in aqueous solution with one or more surfactants. It is possible to form micron or below micron size particles without surfactants, as monomer or prepolymer in solution can serve as surfactants to disperse the oligmers formed during the polymerization reaction. For instance, if melamine and formaldehyde solution are used as monomers to from MF particles, it is not necessary to use surfactant to achieve monodispersed microparticles. However, when PTT is introduced as one of the monomers to form microparticles, surfactants were found to be beneficial to disperse prepolymer oligomers and thereby produce small and consistently sized microparticles. Surfactants can be chosen from a wide range of ionic or nonionic surfactants, preferably water soluble or dispersible surfactants. Surfactants can be used jointly with other surfactants or stabilizing agents. In particular, sodium dodecyl sulfate (SDS) and gum arabic were used as surfactants. Thus in some embodiments the surfactants comprise SDS or gum arabic or both. In some embodiments, the surfactants are at a combined concentration of greater than or equal to 1% by weight in the reaction to form a water-soluble prepolymer in solution in water-miscible solvent A from a mixture of reactants.

In particular embodiments, the polymer comprises melamine residues.

In particular embodiments, the polymer comprises residues of PTT.

In particular embodiments, the polymer comprises residues of a monomer with a plurality of mercapto groups.

In particular embodiments, the polymer comprises residues of a monomor with at least three mercapto groups.

In particular embodiments, the polymer comprises residues of a monomer with at least three arms that contain ester, thioester, anhydride, amide, or orthoester bonds. In particular embodiments, the polymer comprises residues of a monomer with at least three arms that contain ester, thioester, or anhydride bonds.

In particular embodiments, most of the microparticles formed in the reaction have a diameter below 25 microns. In particular embodiments of the compositions of the invention, most of the microparticles have a diameter below 25 microns.

In specific embodiments, the active agent or active agents comprise a corrosion indicator. A corrosion indicator is a material undergoing a transformation through its interaction with the corrosion process. Such transformations can potentially be used for indicating and detecting corrosion damage. Since corrosion of metals is an electrochemical process that produces corrosion products, such as metal ions ($Fe^{2+}$, $Fe^{3+}$, $Al^{3+}$, etc) and/or produces pH changes through localized oxidation/reduction reactions, many of the corrosion indicators are compounds that change color or fluorescent properties (i.e. changes from non-fluorescent to fluorescent states), upon oxidization or reduction, complexing with metal ions, or pH changes.

As described above, pH indicators can be used as corrosion indicators. One example of a pH indicator that is suitable to be used as corrosion indicator is phenolphthalein (phph), which is a pH indicator through color change. Another example of a pH indicator is fluorescein, which is a pH indicator through fluorescent state changes. Further examples of pH indicators are: fluorescein derivatives, the seminaphthorhodafluors, and 8-Hydroxypyrene-1,3,6-trisulfonic acid, bromothymol blue, phenol red, cresol red, and neutral red.

Similarly, ion indicators can be used as corrosion indicators. Tiron (4,5-dihydroxy-1,3-benzenedisulfonic acid disodium salt), FERROZINE (Sodium 3-(pyridin-2-yl)-1,2,4-triazine-5,6-diyl]bis(benzene-4,4'-sulphonate) hydrate, and 1,10-Phenanthroline are some examples of iron ion indicators, through color changes. 8-hydroxyquinoline-5-sulfonic acid is an example of an aluminum indicator through fluorescent changes. Further examples of ion indicators are: potassium ferricyanide, sulfosalicyclic acid, Ammonium sulfocyanide, Xylenol orange, Methylthymol blue, Chalcone, Chromazurol S, Eriochrome black T, 1-(2-Pyridylazo)-2-naphthol, Pyrocatechol violet, Zincon, Sodium alizarinsulfonate, Hematoxylin, Phen Green FL, calcein, rhodamine B-[(1,10-phenanthrolin-5-yl)aminocarbonyl]benzylester, 8-hydroxyquinoline (oxine) and Oxine derivatives, phenylfluorone, Lumogallion, morin, Calcofluor, and Schiff-base compounds derived from substituted aminoanthraquinones and salicylaldehyde (and terephaldehyde).

Redox indicators can also be used as corrosion indicators, such as: Nitrophenanthroline, N-Phenylanthranilic acid, 1,10-Phenanthroline, N-Ethoxychrysoidine, 2,2'-Bipyridine, 5,6-Dimethylphenanthroline, o-Dianisidine, Sodium diphenylamine sulfonate, Diphenylbenzidine, Diphenylamine, Viologen, Sodium 2,6-Dibromophenol-indophenol, Sodium o-Cresol indophenol, Thionine, Methylene blue, Indigotetrasulfonic acid, Indigotrisulfonic acid, Indigo carmine, Indigomono sulfonic acid, Phenosafranin, Safranin, and Neutral red.

One of the advantages of the microparticles formula is its potential to encapsulate an active agent or active agents that can be used as a corrosion indicator, because the cathodic corrosion reaction produces hydroxide ions.

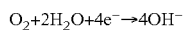

$$O_2+2H_2O+4e^-\rightarrow 4OH^-$$

In one embodiment, the active agent or active agents comprise phph. This becomes colored in alakaline pHs and is colorless at neutral or acidic pHs.

The term "pH indicator" refers to a compound that produces a visible change in color or produces visible fluorescence (when illuminated with visible or ultraviolet light) in response to a change in pH. The term "corrosion indicator" refers to a compound that produces a visible color or produces visible fluorescence (when illuminated with visible or ultraviolet light) when it contacts corroded metal of some sort. Many corrosion indicators are pH indicators. Some corrosion indicators are indicators of the presence of metal ions or are redox indicators.

The high concentration of active agent achieved in the microparticles of the invention is due largely to the active agent being more soluble in solvent B than it is in solvent A (which is typically water) or in oil. Agents that have low solubility in water and oil cannot be easily introduced in high concentrations in microcapsules formed from either oil-in-water emulsions or water-in-oil emulsions. But they are incorporated at much higher concentrations in the microparticles of the present invention, where the active agents are dissolved in a water-miscible solvent B.

Thus, in particular preferred embodiments, the active agent or active agents are more soluble in solvent B than in water or toluene. In specific embodiments, they are more soluble in ethanol than in water or toluene, or more soluble in THF than in water or toluene. In specific embodiments, the active agent or active agents are more soluble in solvent B than in water. In specific embodiments, they are more soluble in ethanol than in water or more soluble in THF than in water.

In other embodiments, the active agent or active agents are more soluble in Solvent B than in Solvent A.

In some embodiments, acid is used to catalyze the polymerization. If the active agent is also an acid, it can perform the role of catalyzing the polymerization. In an example below, for instance, the corrosion inhibitor phenylphosphonic acid (PPA) is used as the active agent and to catalyze the polycondensation step.

Thus, in some embodiments, the active agent or active agents comprise an acidic active agent that catalyzes the polycondensation.

In specific embodiments, the active agent or active agents comprise a corrosion inhibitor. In a specific example, the corrosion inhibitor is PPA.

In other embodiments, the corrosion inhibitors are molybdate, arsenite, arsenate, nitrite, nitrate, phosphate, borate, silicate, vanadate, cerium and other rare earth salts, Sodium tannte, thiourea bezotriazole, film forming polyamine, 3,5 diaminobenzoic acid, sarcosine, potassium oxalate, phosphonic acid, 2-mercaptobenzothiazole, thiourea, 2-mercaptobenzimidazole, 8-hydroxyquinoline, salicylaldoxime, quinaldic acid, 2-(benzothiazol-2-ylsulfanyl)-succinic acid, and benzotriazole.

In particular embodiments of the compositions, compositions are adapted for coating an object (e.g., are coating compositions). The compositions may for instance be paints or, in a more specific case, a latex paint.

In particular embodiments, the composition comprises polyurethane.

In particular embodiments, the composition is a latex composition.

In particular embodiments, the composition comprises epoxy.

In particular embodiments, the composition is a coating on a metal object.

Another embodiment of the invention is a metal object partially or fully coated with a composition of the invention.

One embodiment of the invention provides a method of detecting corrosion comprising: (a) obtaining a metal object partially or fully coated with a coating composition comprising microparticles, the microparticles comprising: a polymer matrix and an active agent or active agents dispersed in the polymer matrix; wherein the active agent or active agents are one or more corrosion indicators; wherein the polymer backbone or a cross-linking segment of the polymer matrix is susceptible to hydrolysis in base; and (b) monitoring the object for visible changes of color or fluorescence from the one or more corrosion indicators that would indicate corrosion.

In specific embodiments of the metal objects, the methods of detecting corrosion on a metal object, and the methods of producing a corrosion-detecting metal object, the metal object is a screw, bolt, or nut. In other embodiments, the metal object may be a rivet, a rivet shaft, a rivet head, a rivet tail, or any other metal fastener.

One embodiment of the invention involves detecting corrosion at a distance from the primary site of corrosion. This may be corrosion that is hidden, for instance, crevice corrosion that is not visible from the surface of the structure. In particular, the corrosion indicator compositions can be coated on the head of screw, bolt, rivet, or any other metal fastener (cathodic sites) and detect corrosion on the shaft of the screw, bolt, rivet, or any other metal fastener (anodic sites); for example underneath the nut, where the nut contacts the bolt or screw or in the substrate where the substrate contacts the screw, bolt, rivet, or any other metal fastener.

Thus, in a particular embodiment of the method of detecting corrosion, the metal object is a screw, bolt, or rivet having a shaft and a head, wherein the coating composition is on the head of the screw, bolt, or rivet; wherein the method comprises monitoring the screw, bolt, or rivet for visible changes on the head that indicates corrosion on the shaft.

EXAMPLE 1

Synthesis of Water Soluble pH-Sensitive MFPTT Prepolymer

An Melamine (M), Formaldehyde (F), Pentaerythritol Tetra (3-Mercaptopropionate) (PTT) (MFPTT) pH-sensitive particle synthesis process was developed after the discovery of a water soluble pH-sensitive prepolymer that can be utilized to modify a polycondensation process for preparing monodispersed melamine-formaldehyde microspheres.

It was found that a reaction product of MFPTT is water soluble at least at some stage of the reaction. And this water soluble prepolymer (or, more likely, a mixture of prepolymers) is used as wall material for forming pH-sensitive microcapsules as well as pH-sensitive microparticles.

From a typical formula for pH-sensitive microcapsules based on melamine formaldehyde and PTT, the proper molar ratio of M, F, and PTT was selected at the following ratio:

M:F:PTT=1:3.32:0.172

Figure 1B:
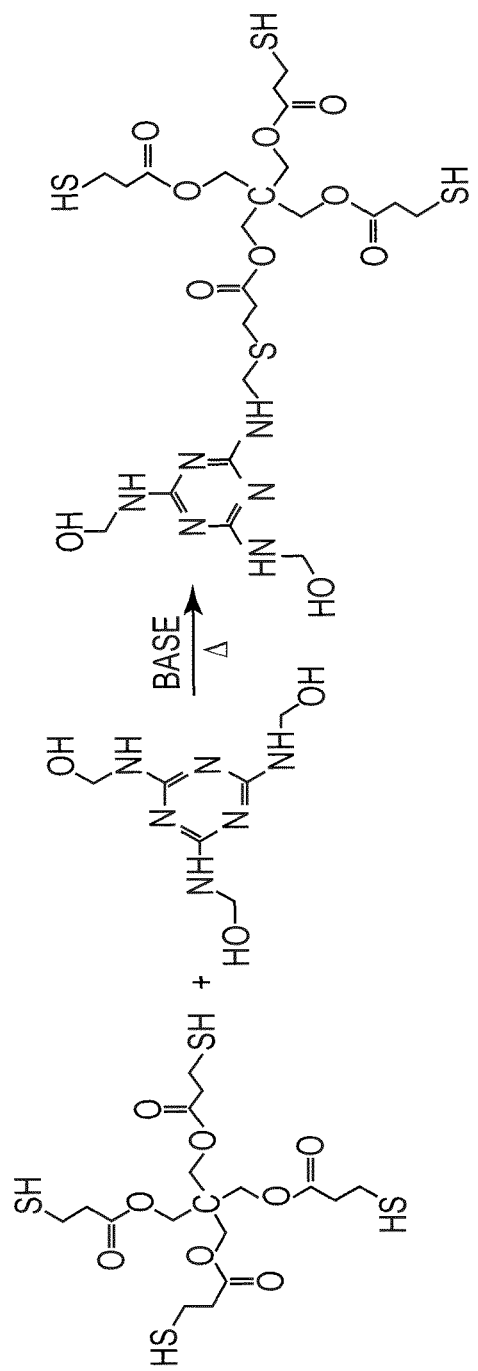
Figure 1C:
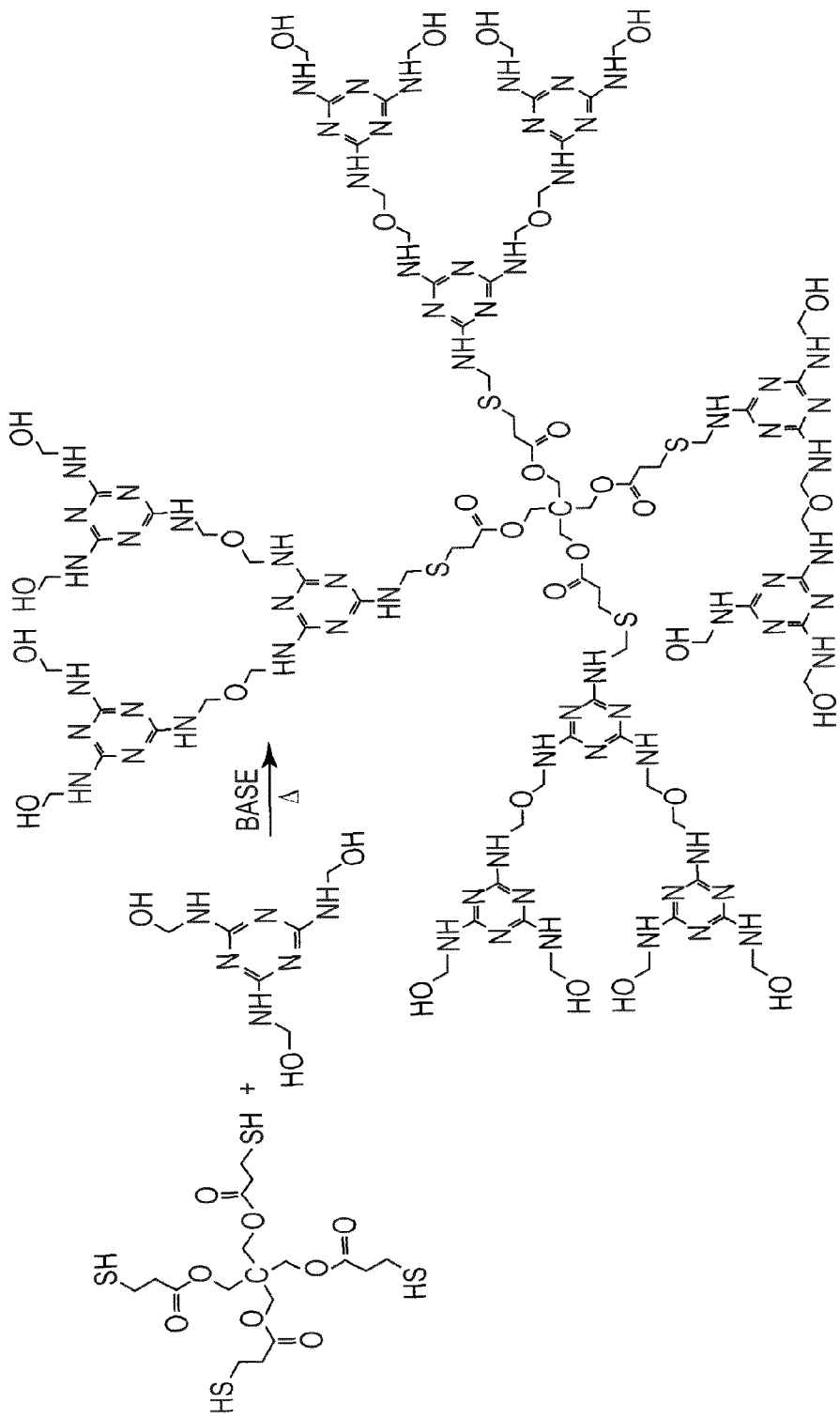

The ratio between M and F is close to 1:3; the reaction between them is represented in FIG. 1A, where M and F form trimethylolmelamine (MF). While the ratio between M and PTT is close to 6 to 1, the reaction between MF and PTT, which helps PTT to dissolve in water, is likely the reaction of FIG. 1B, rather than the reaction of FIG. 1C, as the reaction product of FIG. 1C seems to be too big to be water soluble, while the reaction of FIG. 1B alone would help PTT become water soluble. Thus at the reaction stage when PTT dissolves in water, the reaction mixture includes MF, and MFPTT. Further heating after PTT is dissolved in water will eventually lead to formation of a non-water-soluble product. The synthesis of the prepolymer is shown in FIGS. 1A-1C.

Development of MFPTT Particle Formula
Synthesis of MF Particles:

In order to make MFPTT phph particles, MF particle synthesis processes in the literature were reviewed and some compared experimentally; then MFPTT particles were synthesized using a selected processes.

Several synthesis processes for preparing monodispersed MF particles were compared, and some processes were carried out in the lab to compare with the MFPTT particle synthesis process. One example of an MF particle synthesis process used the following starting formula.

TABLE 1

Formula for MF particle.

| Reagent | Mass (g) |
| --- | --- |
| Water | 200 |
| Formaldehyde (37%) | 9.8 |
| Melamine | 2.5 |
| Butyric acid | 2 |

Figure 2:
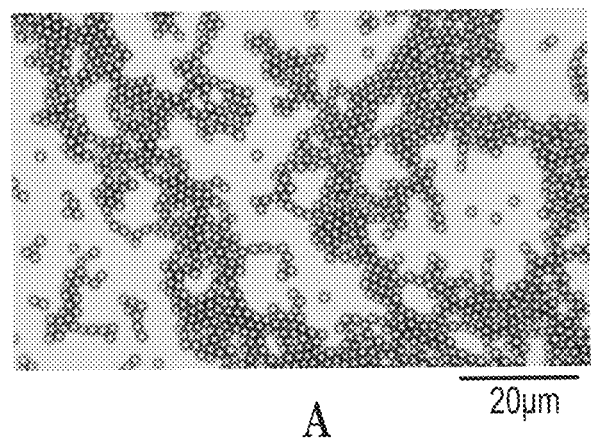
FIG. 2 is a micrograph of MF particles prepared as described in Example 1.
Figure 2:
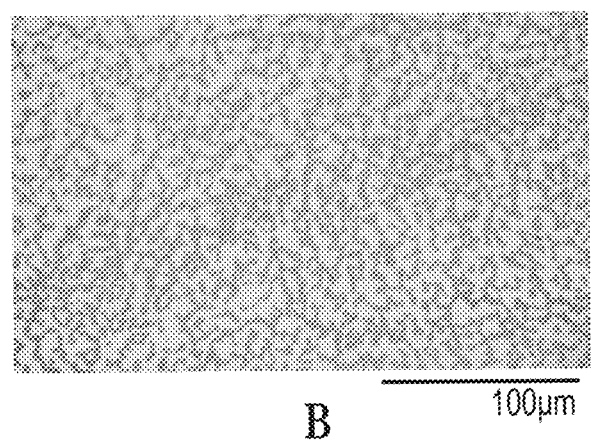

A solution of formaldehyde (9.8 g, 37%) and water (200 ml) was prepared and heated to 80° C. Subsequently, melamine (2.5 g) was added with stirring. When the melamine was completely dissolved, butyric acid (2 ml) was added as a catalyst for the polycondensation reaction between formaldehyde and melamine. Spherical droplets of MF resin were formed as a result of surface tension, which were subsequently transformed into solid particles. A micrograph showing microparticles formed as described in this section is shown in FIG. 2.

Development of MFPTT Microparticle Formulation: Our Approach

Trial Formulation Without Surfactant

A similar formula was used to synthesize MFPTT particles, as shown in Table 2.

TABLE 2

Formula for MF particle.

| Reagent | Mass (g) |
| --- | --- |
| Water | 200 |
| Formaldehyde (37%) | 9.8 |
| Melamine | 2.5 |
| PTT | 2 |
| Citric acid | 2 |

The process did not work well. M/F/PTT formed water-soluble prepolymer but, after acid was added, the MF/PTT oligomers appeared as big, sticky, oily droplets that settled down to the bottom of the container or attached to the wall of the container. This was unlike the MF system, where the MF oligomers served as dispersing agents for themselves. After a day, there were solid particles formed, although the majority of the prepolymer agglomerated together. It was concluded that the MF/PTT system needs external surfactants to form emulsion before the particle formation.

EXAMPLE 2

Formulation With Surfactant

Another formula was used to synthesize MFPTT particles with surfactants.

TABLE 3

Formula for MFPTT particle.

| Reagent | Mass (g) |
| --- | --- |
| Water | 90 |
| Formaldehyde (37%) | 9.6 |
| Melamine | 4.5 |
| PTT | 3.2 |

TABLE 3-continued

Formula for MFPTT particle.

| Reagent | Mass (g) |
|---|---|
| SDS | 1.5 |
| Gum arabic | 1.5 |
| pTSA | |

Two synthesis processes were tested based on this formula: with and without acid catalyst.

Figure 3:
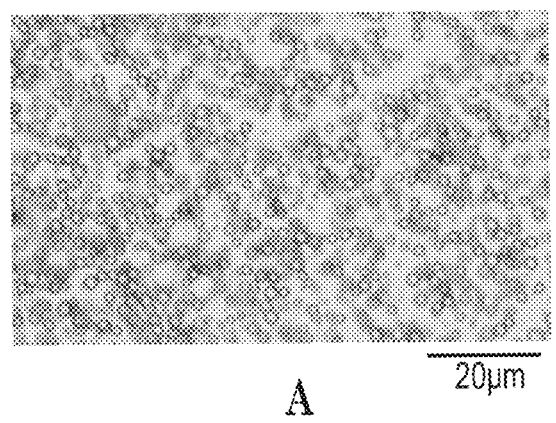
FIG. 3 is a micrograph of MFPTT droplets (panel A) and microparticles (panel B) as prepared in Test 1 of Example 2.
Figure 3:
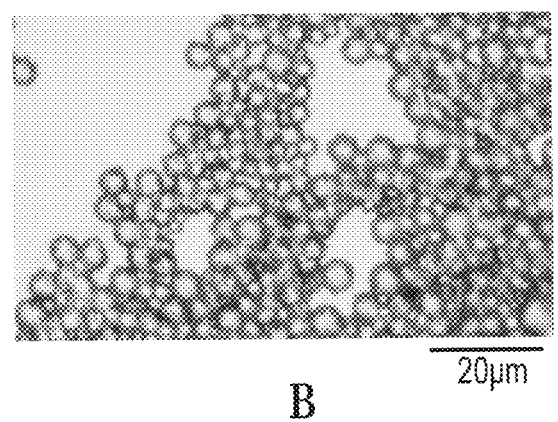

The first test was done without any acid catalyst. The starting formula in Table 3 was followed, without using acid (p-toluene sulfonic acid (pTSA)). The formula mixture was heated at 65° C. for 2 hours, before the experiment ended. The resulting particle size was not homogenous, the smaller particles seemed to attach onto the bigger ones. The surfactant did keep the oligomers apart from each other, so there were no sticky oligomers formed at the bottom of the beaker or on the wall of the beaker. FIG. 3 shows MFPTT droplets (panel A) and microparticles (panel B) formed under this test 1 process viewed under an optical microscope.

Figure 4:
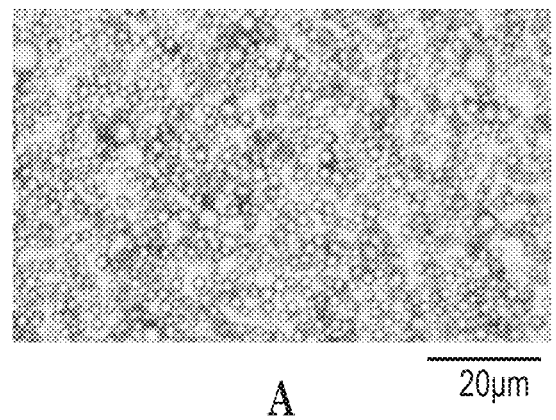
FIG. 4 is a micrograph of MFPTT droplets (panel A) and solidified microparticles (panel B) as prepared in Test 2 of Example 2.
Figure 4:
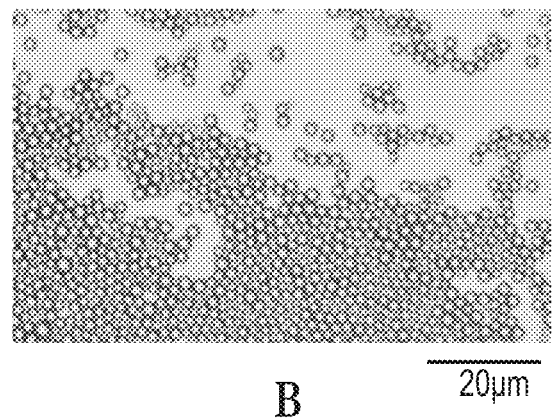

The second test was done with acid as catalyst. The starting formula in Table 3 was followed. pTSA was added until the pH reached 6. Heating was stopped after acid was added. Particle size appeared to be much more homogeneous. (As shown in FIG. 4).

Based on these test results, it is concluded that SDS and gum arabic (at ~3 wt %) are effective surfactants for the dispersion of MFPTT oligomers. Further tests were carried out to test the effect of surfactant concentration. It was found that when these surfactants are present with a combined concentration equal to or greater than 1 wt % they are effective to prevent oligomers from clustering.

To summarize these results, pH-sensitive microparticles were synthesized using water soluble pH-sensitive prepolymer, and the microparticles were homogenous in size. The particle size was below 5 microns, suitable for coating applications.

The pH-sensitive microparticles can be further adapted to form particles containing active agents for various pH controlled-release application. Some potential applications include pH-sensitive microparticles containing corrosion indicators and inhibitors for coating applications.

EXAMPLE 3 pH-Sensitive Microparticles With Corrosion Indicator

Several microcapsule formulas have been developed over time for corrosion indication functions: oilcore phph microcapsules formed through an interfacial polymerization process; watercore phph microcapsules formed through interfacial polymerization; and oilcore phph microcapsules formed through in-situ polymerization. These microcapsule formulas all provide pH and corrosion indication functions in solution, in gel, and in paint through color change. The intensity of the color change is largely dictated by the amount of phph present.

In order to increase the amount of phph content, we developed a pH-sensitive microparticle formula with active agent phph dispersed in polymer strands. These microparticles were found to provide the strongest color change due to their high phph content. There are two advantages associated with this phph microparticle formula: the first is its high phph content, up to 25 to 30 wt %; the second is that the synthesis process produces a free-flowing powder with particle size below 25 microns, which is easy to disperse into paint systems. This synthesis process is described below.

Figure 5:
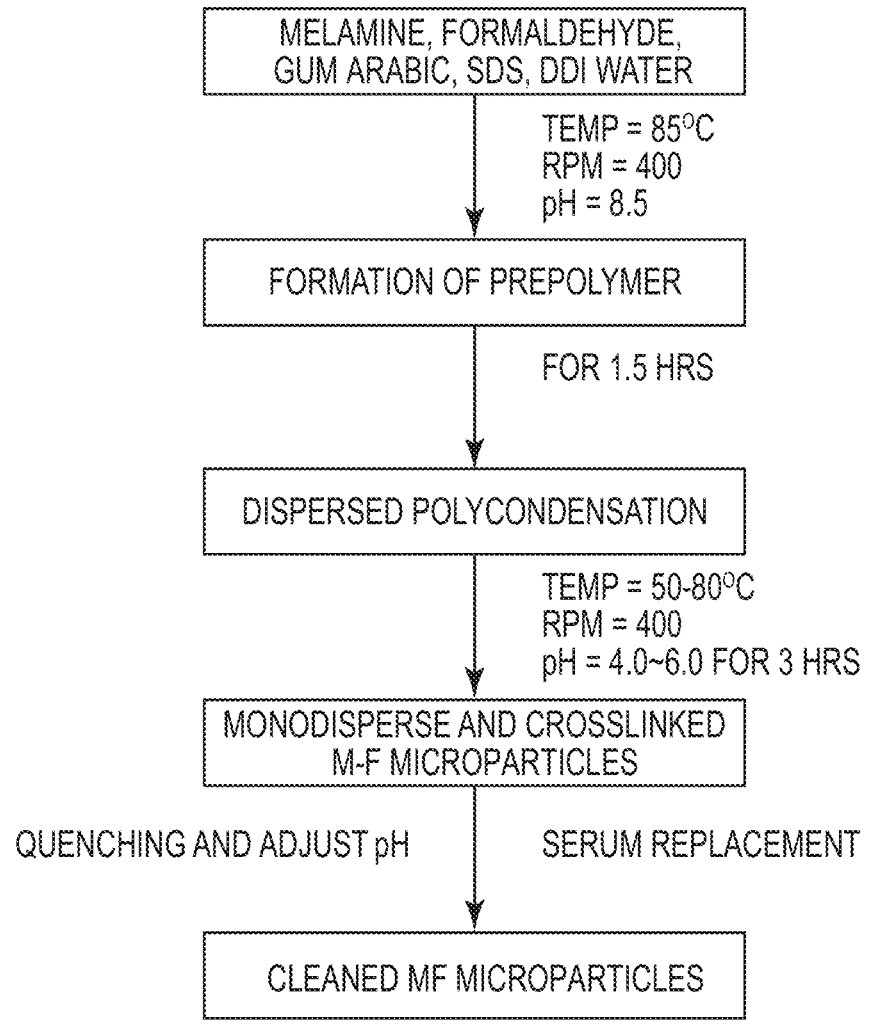
FIG. 5 is a flowchart showing the steps in synthesis of MF microparticles prepared via dispersed polycondensation, as described in Example 3.

MFPTT phph particle synthesis process was developed after the water-soluble pH-sensitive prepolymer was discovered and utilized to modify a polycondensation process for preparing monodispersed melamine-formaldehyde microspheres. It is a 2-step process; first is an addition reaction of M and F under basic conditions, and then the polycondensation reaction under acid conditions (See FIG. 5.). After that, we ended the reaction, cleaned, washed, and harvested the microparticles.

Synthesis of MFPTT phph Microparticle

Figure 6:
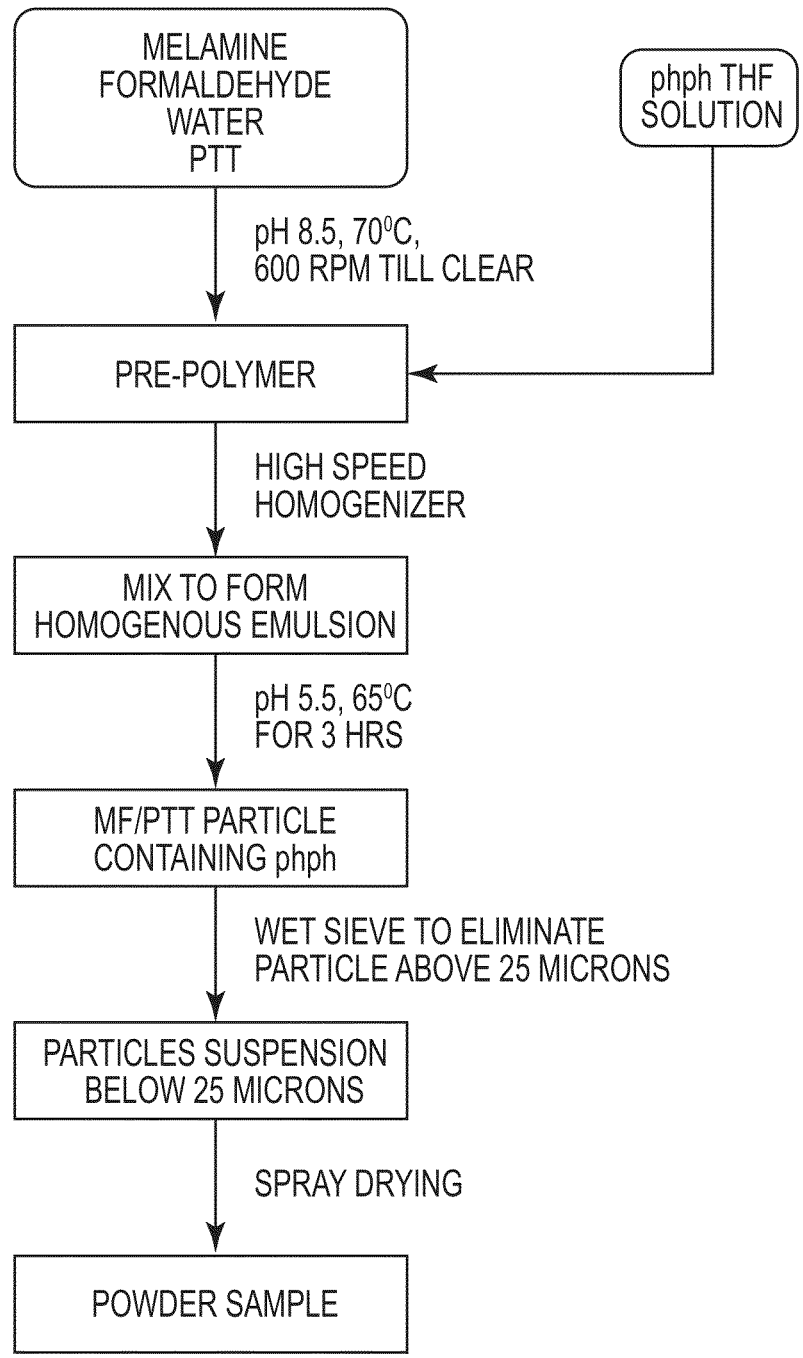
FIG. 6 is a flowchart showing the synthesis process for MFPTT phenolphthalein (phph) microparticles prepared as described in Example 3.

There are two major differences between the processes of MF particle (FIG. 5) and the MFPTT phph particle synthesis (See FIG. 6).

(1) In the addition reaction stage, the prepolymer is not just made from M and F, it contains a third starting material that provides the pH-sensitive ester group.

(2) In the polycondensation step, the THF solution of phph is introduced to incorporate phph into the particles to be formed.

This process resulted in MFPTT phph particles below 25 microns in a free-flowing powder form, and with a phph content as high as 25 to 30 wt %. But the formula also produced some MFPTT phph particles greater than 25 microns as a by-product. The fine (below 25 microns) and coarse (greater than 25 microns) particle ratio is about 7 to 3. The overall recovery rate, (the total particle formation including fine and coarse) ranged from 75 to 90%.

Further Optimization of MFPTT Particle Formula

Further studies were carried out to reduce the by-product, as well as improve the overall recovery rate, i.e., the total particle formation from the same starting formula.

After revisiting and gaining a better understanding of MF and MFPTT particle formations, we started to optimize the formulation of MFPTT phph particles.

Current Formula for MFPTT phph Microparticle

First, the existing formula (See Table 4) was examined. If all phph is encapsulated by all MFPTT particles, then there should be about 30% phph in the particle, which is consistent with titration results. There is likely a loss of phph during the addition process, and there is likely a loss of formaldehyde during the polymerization process.

TABLE 4

Formula for MFPTT phph particle.

| Reagent | Mass (g) |
|---|---|
| MFPTT resin | |
| Water | 900 |
| Melamine | 45 |
| Formaldehyde (37%) | 96 |
| PTT | 32.5 |
| Surfactant: SDS/Gum arabic | 15/15 |
| Phph Solution | |
| THF | 133 |
| phph | 50 |
| Catalyst | |
| pTSA | pH 5.5-6 |

Figure 7:
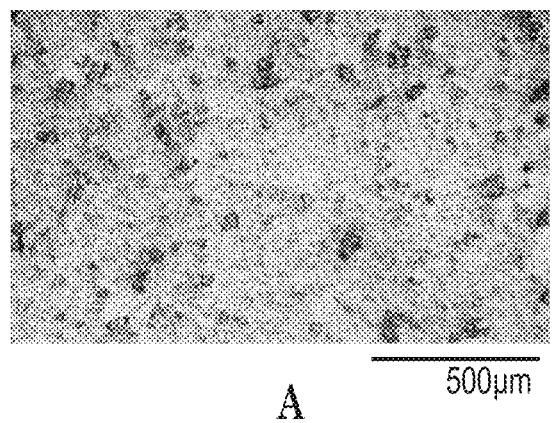
FIG. 7 is a series of micrographs of MFPTT phph microparticles prepared as described in Example 3.
Figure 7:
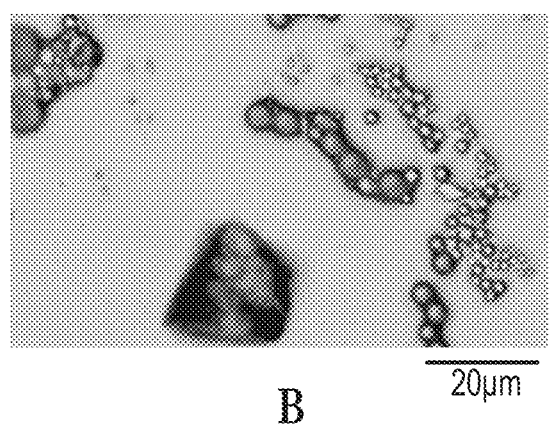

This formula produced a mixture of fine particles and spherical particles about 2-3 microns in size, and also some larger clusters and some of what appeared to be coated phph crystals as shown in FIG. 7.

Effect of the Harvesting Process on Particle Size

To get more fine particles, the post treatment is as important as the synthesis formula. It was found that while the post-synthesis mixture contained some larger particles, when the mixture was simply left to air dry or oven dry, the dried sample contained more of the larger particles. It was assumed that the surface of the particle contains many reactive sites, and this causes particles to fuse together during drying. So we decided to heat treat the particles for complete conversion possibly with butanol as a capping agent to terminate the active sites on the surface of the particles. Unfortunately, the heat treatments, with or without a capping agent, resulted in many more large particles due to residual MFPTT prepolymer still in the solution, and the heat treatment caused it to form a solid and fused smaller particles together. To correct this, we washed the particles before curing to eliminate excess MFPTT and then spray dried them. It was found the washing process could be replaced by simply letting the suspension settle and then getting rid of the top clear solution. Some experiments were carried out, and it was found that eliminating prepolymer left in the product, by washing and settling, resulted in more homogenous and smaller particle sizes.

The updated process includes the following four steps:
(1) Synthesizing the particle
(2) Wet sieving: separate out anything that is above 25 microns
(3) Prepolymer separating: let the suspension of particles smaller than 25 microns settle, and remove the top clear solution which may contain prepolymer
(4) Spray drying: re-disperse the particles into water and spray dry to get free flowing powder.

Using the existing formula and four-step process, and adding phph slowly (over about 10 minutes), the final product of one test is shown in Table 5.

TABLE 5

An example of final product using existing formula and separation process

| | Mass (g) |
|---|---|
| Particles greater than 25 microns | 38 |
| Particles smaller than 25 microns | 89.25 |
| MFPTT + phph | 167 |
| Recovery rate | (38 + 89.25)/167 = 76% |
| Fine particle % | 89.25/(89.25 + 38) = 70% |

EXAMPLE 4

Further Optimization for Better Size Distribution
Preliminary Tests

To further improve the formula, several of the possible influencing factors were analyzed:
(1) Speed at which phph/THF solution is added
(2) THF amount
(3) heating temperature (how quickly THF evaporates)
To find the effect of each factor, four tests were compared:
(1) control
(2) control with slower addition of phph (about 10 min)
(3) control with slower addition of 2×THF (about 20 min)
(4) control with slower addition of 2×THF and no heating.

A closer look also reveals that although slower addition of phph with 2×THF (double THF amount) seems to reduce the amount of bigger clusters, they were not eliminated. It was also observed that the phph/THF solution forms emulsion droplets when it is added into the mixture. A more efficient surfactant system to disperse THF/phph could better solve the problem.

THF/phph Emulsion

Figure 8:
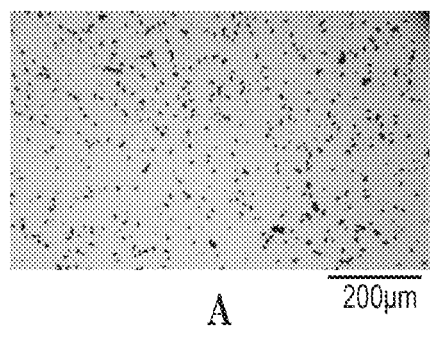
FIG. 8 is a series of micrographs of a phph/tetrahydrofuran (THF) emulsion in water according to Test 1 of Table 6 in Example 4.
Figure 8:
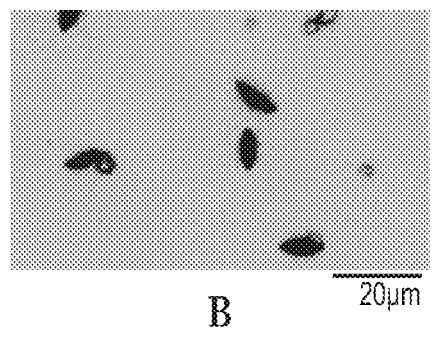
Figure 8:
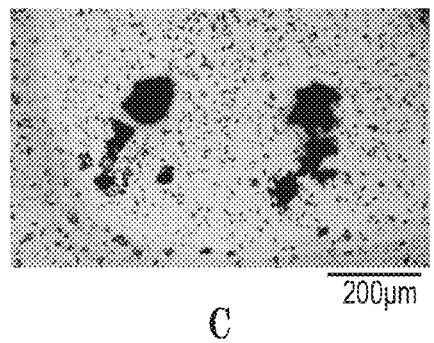
Figure 8:
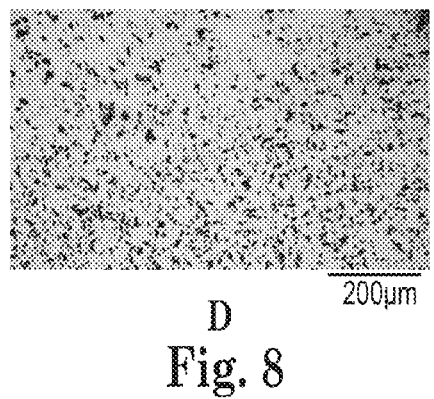
Figure 9:
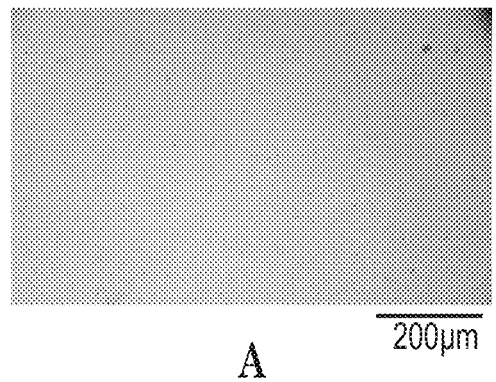
FIG. 9 is a series of micrographs of a phph/THF emulsion in water according to Test 2 of Table 6 in Example 4.
Figure 9:
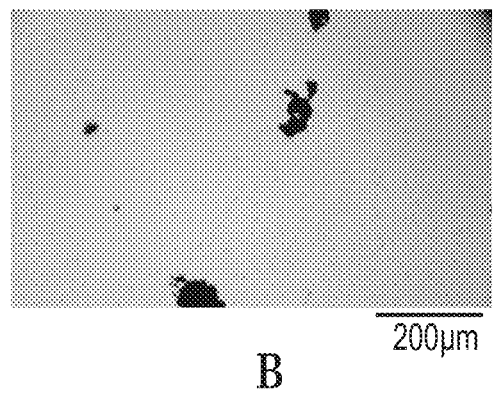
Figure 10:
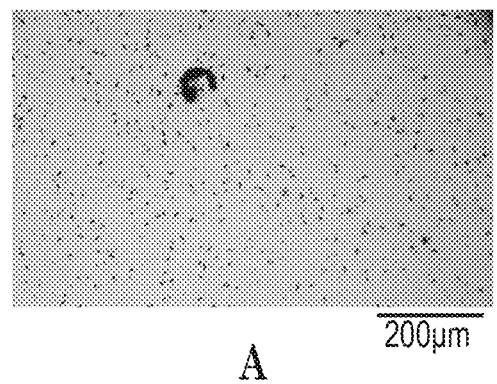
FIG. 10 is a series of micrographs of a phph/THF emulsion in water according to Test 3 of Table 6 in Example 4.
Figure 10:
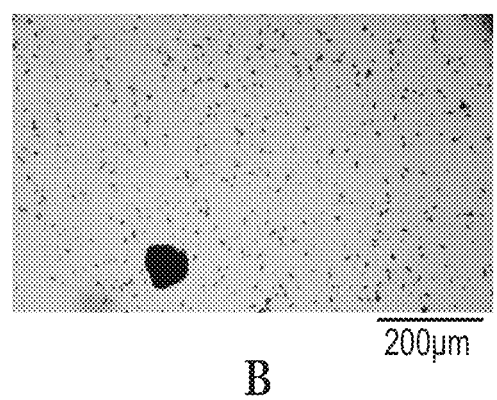

An extensive test to find a better surfactant to disperse THF/phph in water was conducted. Test results show that Tween 80 seems to be a good surfactant, so three tests were done: (1) disperse THF/phph into 3% Tween 80; (2) 5% Tween 80; and (3) 5% Tween 80 and twice the amount of water (See Table 6). Micrographs of the particles resulting from tests 1, 2, and 3 are shown, respectively, in FIGS. 8, 9, and 10.

TABLE 6

THF phph emulsion tests.

| Mass (g) | Test 1 | Test 2 | Test 3 |
|---|---|---|---|
| phph | 0.8 | 0.8 | 0.8 |
| THF | 4 | 4 | 4 |
| Tween 80 | 0.5 | 0.9 | 0.9 |
| Water | 18 | 18 | 36 |

All three tests resulted in dispersed phph in water, and increasing the surfactant concentration resulted in smaller phph particles in dispersion. Increasing the water/THF ratio resulted in fewer bigger clusters, although these tested formulas did not eliminate bigger particles/clusters completely. Overall, the emulsion formula provided great improvement in phph dispersion.

MFPTT phph Particles Using THF Emulsion

Various THF/water emulsion formulas have been tested in MFPTT phph particle formulas, and they all generally helped reduce the amount of bigger particles formed and provide the desired optimization for the phph particle formulas. Representative testing results are reported in the following sections.

Figure 11:
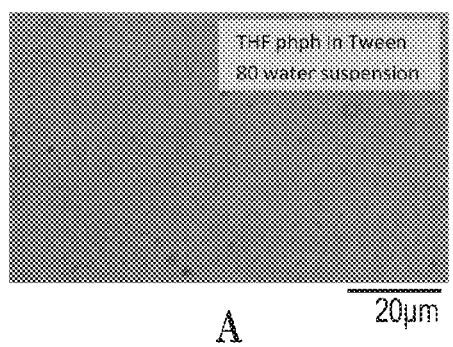
FIG. 11 is a series of micrographs of the reaction mixture at certain stages of the synthesis of MFPTT phph microparticles according to Table 7 in Example 4. Panel A is the phph suspension with THF in Tween 80 in water before mixing with the MFPTT resin portion of the reaction mixture. Panel B shows the reaction mixture after half the phph suspension is added. Panels C and D show the reaction mixture after all the phph is added.
Figure 11:
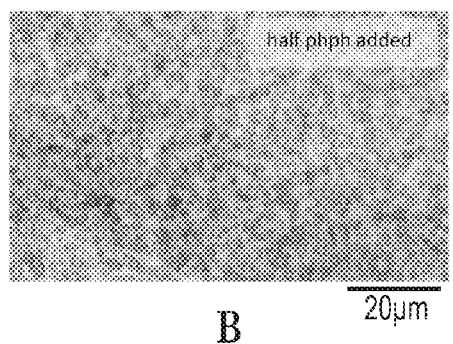
Figure 11:
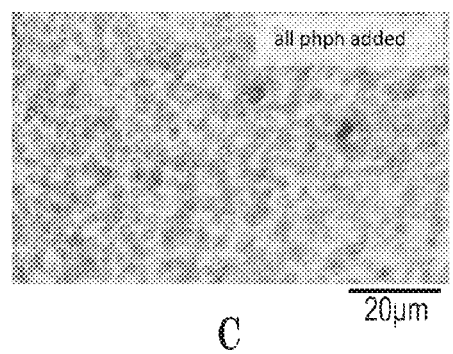
Figure 11:
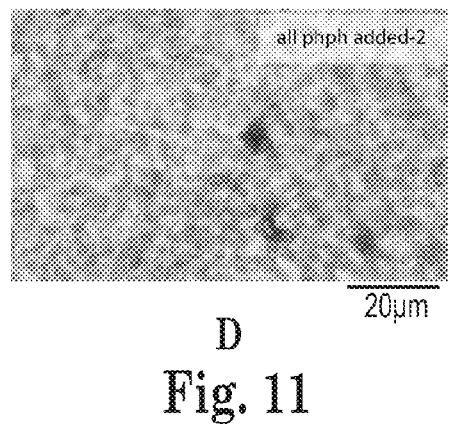

The formula of the first test is shown in Table 7, and the images captured by a digital microscope during the synthesis process show that the THF phph emulsion is homogenous, and the droplet size is small (See FIG. 11). After half the phph was added to the MFPTT prepolymer, no bigger particles were observed; but after all the phph was added, a few bigger particles appeared. It is possible that some THF evaporated during the process, which causes phph crystals to appear.

TABLE 7

MFPTT phph particle formula using THF emulsion.

| Reagent | Mass (g) |
|---|---|
| MFPTT resin | |
| Water | 180 |
| Melamine | 4.5 |
| Formaldehyde (37%) | 9.6 |
| PTT | 3.2 |
| Surfactant: SDS/Gum arabic | 3/3 |
| Phph Suspension | |
| THF | 12 |
| Phph | 5 |
| Water | 90 |
| Tween 80 | 6 |
| Catalyst | |
| pTSA | pH 5.5-6 |

Figure 12:
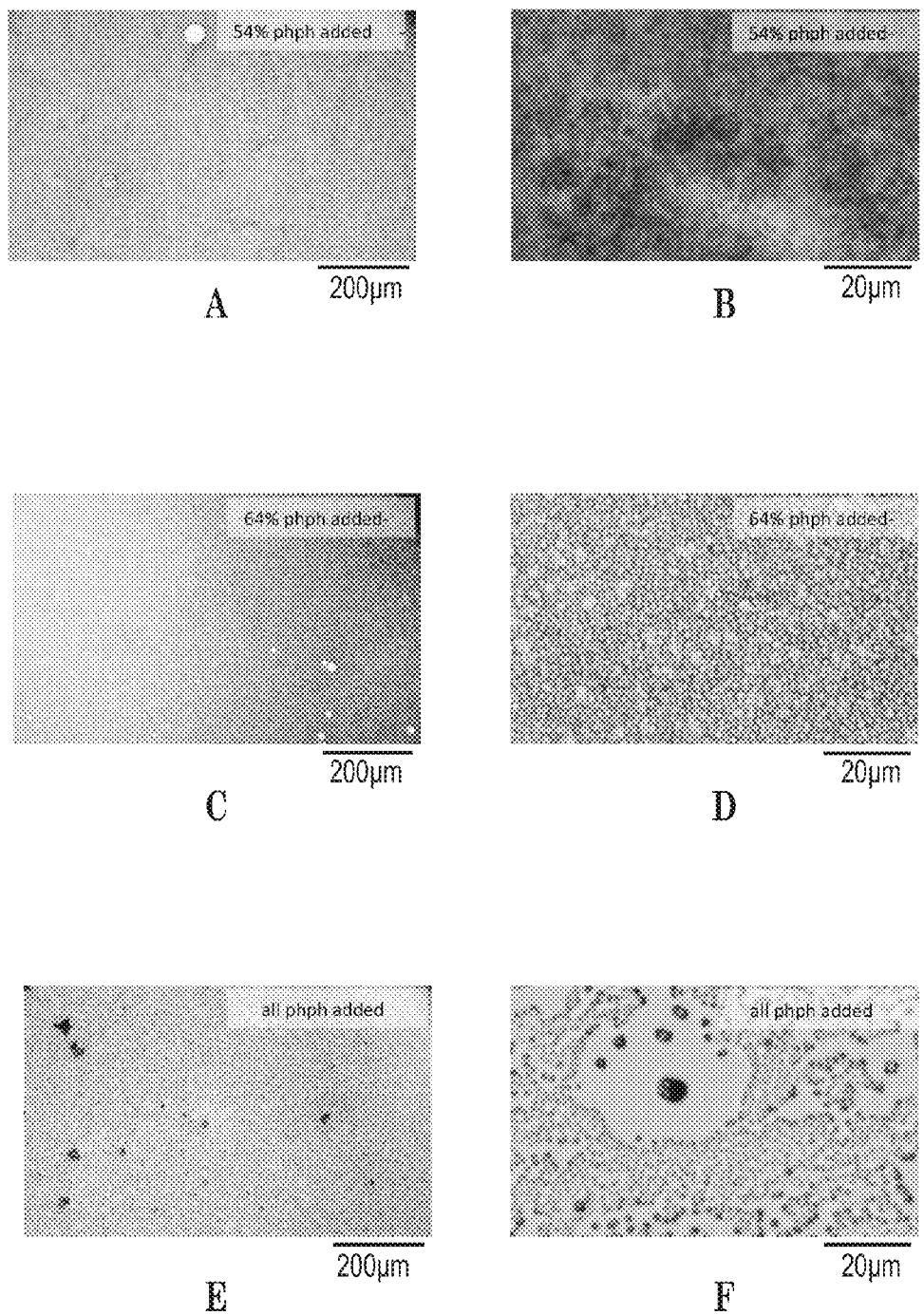
FIG. 12 is a series of micrographs of the reaction mixture at certain stages of the synthesis of MFPTT phph microparticles according to Table 8 in Example 4. Panels A and B show the reaction mixture when 54% of the phph suspension had been added. Panels C and D show the reaction mixture after 64% of the phph suspension was added. Panels E and F show the reaction mixture after all of the phph suspension was added.

The formula of the next test is shown in Table 8. The amount of THF in the phph THF emulsion was increased to avoid phph crystal formation due to THF evaporation (See images in FIG. 12).

TABLE 8

MFPTT phph particle formula using THF emulsion.

| Reagent | Mass (g) |
|---|---|
| MFPTT resin | |
| Water | 180 |
| melamine | 4.5 |
| Formaldehyde (37%) | 9.6 |
| PTT | 3.2 |
| Surfactant: SDS/Gum arabic | 3/3 |
| Phph Suspension | |
| THF | 30 |
| Phph | 5 |
| Water | 90 |
| Tween 80 | 3 |
| Catalyst | |
| pTSA | pH 5.5-6 |

Figure 13:
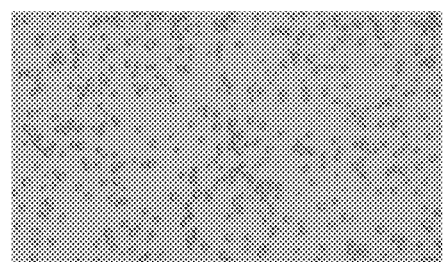
FIG. 13 is a series of micrographs of the reaction mixture at certain stages of the synthesis of MFPTT phph microparticles according to Table 9 in Example 4 where each panel shows the different stages during the process of adding different amounts of phph THF solution up to to a total of 350 ml. The notations on the panels show the proportion of the 350 ml of phph that had been added when the photomicrograph was taken. Panels K and L are photomicrographs taken 30 and 60 minutes respectively after all the phph was added.
Figure 13:
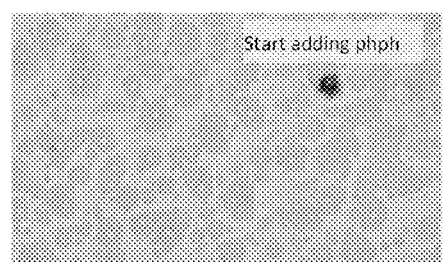
Figure 13:
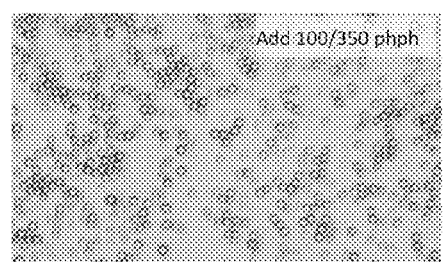
Figure 13:
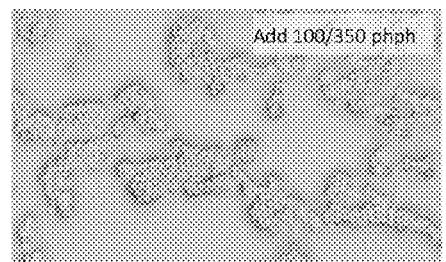
Figure 13:
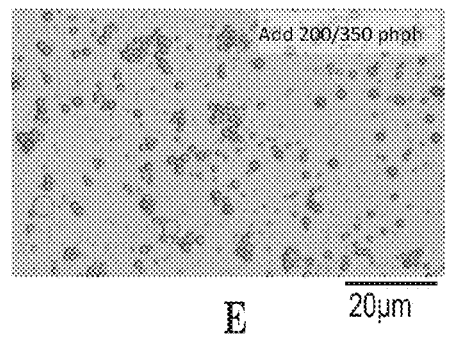
Figure 13:
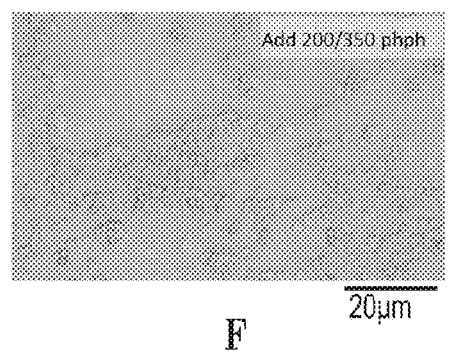
Figure 13:
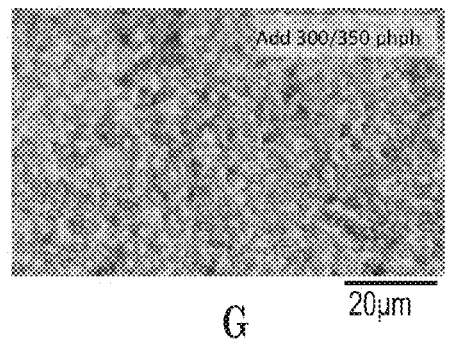
Figure 13:
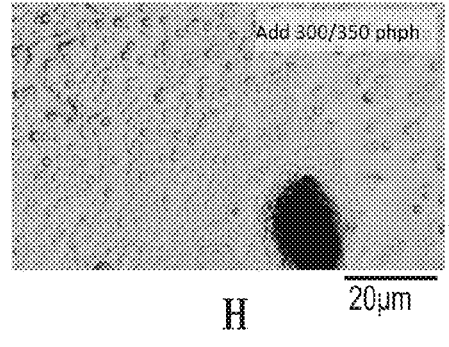
Figure 13:
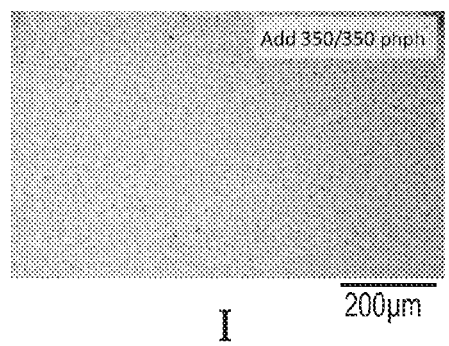
Figure 13:
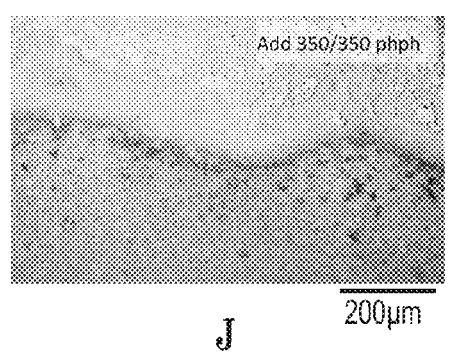
Figure 13:
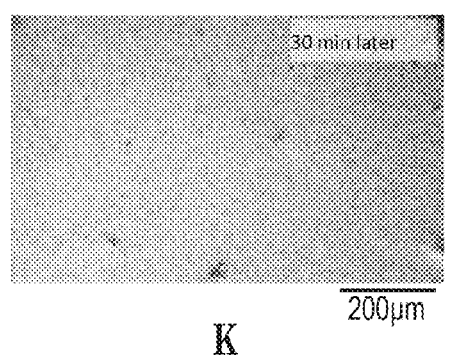
Figure 13:
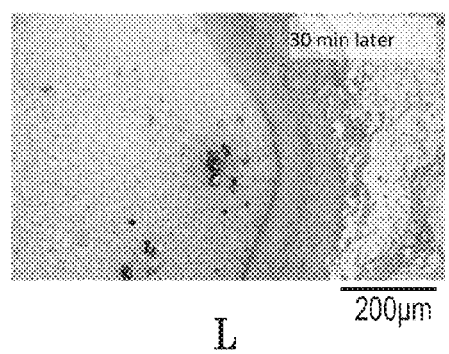

In the next test, the previous test was repeated with a scaled-up formula as shown in Table 9. To better control the process, a micro-pump was used to add phph suspension at a constant rate (16 ml/min). The overall result was very good; there were very few microparticles greater than 25 microns in size (See FIG. 13).

TABLE 9

MFPTT phph particle formula using THF emulsion.

| Reagent | Mass (g) |
|---|---|
| MFPTT resin | |
| Water | 450 |
| Melamine | 11.25 |
| Formaldehyde (37%) | 24 |
| PTT | 8.1 |
| Surfactant: SDS/Gum arabic | 7.5/7.5 |
| phph Suspension | |
| THF | 75 |
| phph | 12.5 |
| Water | 225 |
| Tween80 | 7.5 |
| Catalyst | |
| pTSA | pH 5.5-6 |

As shown in these examples, the formulas that were modified using THF/phph emulsion showed great improvement on the final particle size, and reduced the amount of bigger particles as a by-product.

pH-sensitive microparticles with high corrosion indicator concentration (20 to 30 wt %) were synthesized. The process was optimized to produce particles with small and even particle sizes (appoximately 2 microns).

EXAMPLE 5

Corrosion Indication Using MFPTT phph Microparticles

Figure 14:
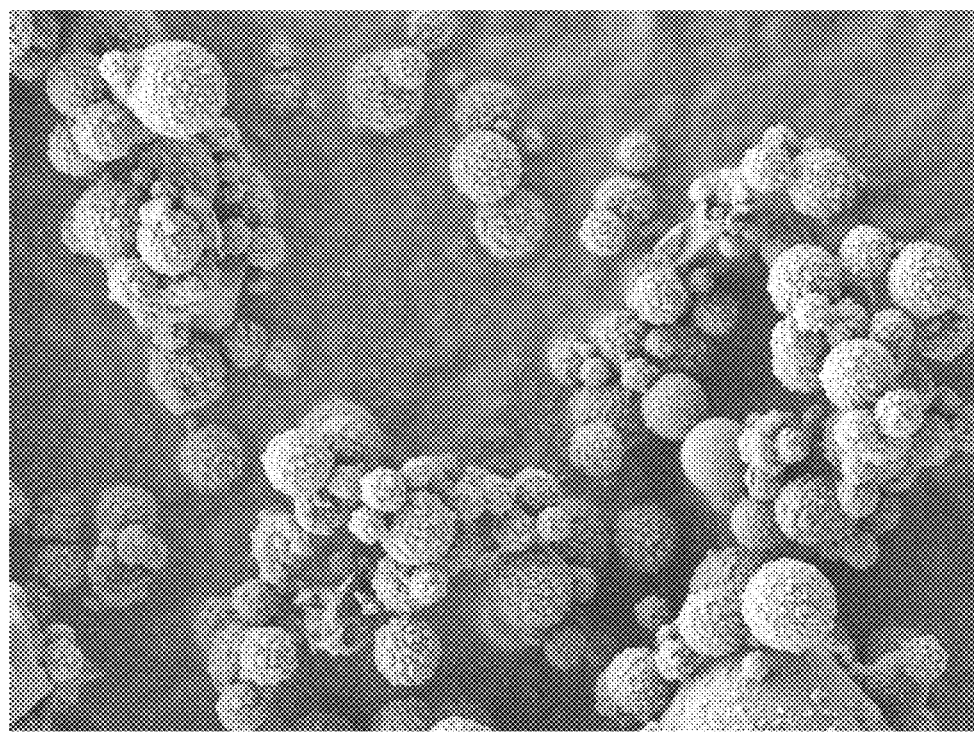
FIG. 14 is a scanning electron microscope (SEM) image of phph-containing microparticles of the invention.

As mentioned above, the intensity of the indicator color change is largely determined by the amount of phph present. Since phph does not dissolve directly in the oil phase or the water phase, its concentration in the microcapsule core is not high enough to provide a color change of the desired intensity to detect corrosion. The phph concentration is about 2 wt % in the oil-core microcapsule and 5 wt % in the water-core microcapsule. But we have found that with the present pH-sensitive microparticles with phph dispersed in the polymer matrix, the amount of incorporated phph increased to up to 30 wt % of the microparticles. FIG. 14 shows a scanning electron microscope (SEM) image of phph microparticles with sizes of 1 to 2 μm.

Early Corrosion Indication

In order to develop a prototype paint formulation for corrosion indication, encapsulated phph was incorporated into different types of coating systems and tested for its effectiveness as a corrosion indicator. Urethane coatings were selected as potential candidates for a prototype corrosion indicating paint formulation (i.e., smart coating). Encapsulated phph was incorporated into a clear urethane coating and its effectiveness as an early corrosion indicating coating, as well as a hidden corrosion detecting coating, was demonstrated experimentally. Detailed information of the test results follow.

Figure 15:
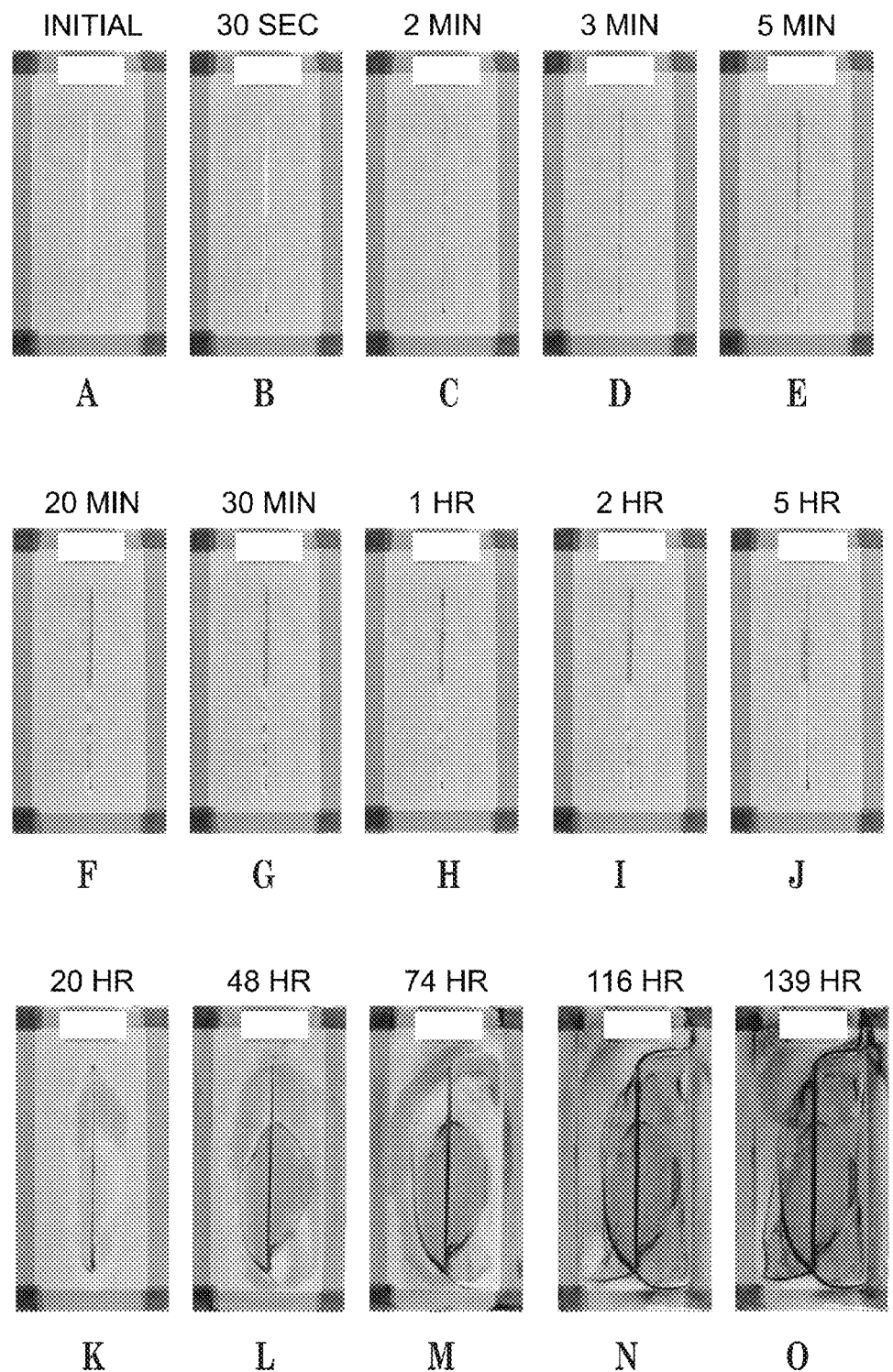
FIG. 15 is a series of photographs showing the results of salt immersion test of steel panels coated with a clear urethane coating containing 10% microparticles with phph corrosion indicator, as described in Example 5.

FIG. 15 shows the results from the salt immersion test of steel panels coated with a clear urethane coating containing 10% of microparticles with corrosion indicator. The panels were scribed and observed for visible changes over time. It was observed that the indicator signaled the onset of corrosion in the scribe in less than 1 minute after immersion, which is considerably earlier than the 2 hours it takes for the typical color of rust to appear.

The early detection of corrosion in various structures has both economic and safety implications. Corrosion damage, when detected early, can potentially be corrected at a much lower cost, by avoiding large scale material and structural repairs and/or replacement, loss of operation time, and loss of productivity. Some corrosion damage could cause catastrophic structural failures, thus in this situation early corrosion detection technology could significantly improve safety.

Detecting Hidden Corrosion

In addition to early corrosion detection, another potential application of the microparticles is to detect hidden corrosion.

Similarly, detection of hidden corrosion is equally important where two metal objects are in contact with each other and a surface of a first metal object and a surface of a second metal object are not visible. A coating that changes color on the visible surface of the first metal object when corrosion starts on either the first or second metal object would be greatly beneficial in early corrosion detection.

Detection of hidden corrosion is based on spatial separation of the anodic corrosion reaction and the cathodic corrosion reaction. Reaction (1) below is a typical anodic corrosion reaction.

$$Fe \rightarrow Fe^{2+} + 2e^- \qquad (1)$$

Reaction (2) below is a typical cathodic corrosion reaction.

$$O_2 + 2H_2O + 4e^- \rightarrow 4OH^- \qquad (2)$$

For localized corrosion such as pitting, crevice, and exfoliation corrosion, this cathodic reaction tends to occur at more accessible locations than the anodic reaction, i.e. nearer to the source of oxygen in the air. This reaction will cause an increase in the local pH at the location where it occurs, so a paint that responds to a pH increase generated by the cathodic reaction will indirectly be sensing corrosion occurring nearby, at the anodic location.

Metal fasteners, such as bolts, screws, and rivets tend to corrode on the hidden shaft area before visible corrosion is seen on the fastener head, nut, or rivet tail. Often, the head and nut/tail are in pristine condition even when significant corrosion has occurred on the shaft. There is no method to identify the degree of corrosion without removing the fastener from service. A coating that changes color on the fastener head or nut/tail when corrosion starts would greatly facilitate the inspection process and increase the safety and reliability of the structure.

The basic pH produced by the reaction is detected as visible color from the phph, which is colorless in acid or neutral pH and colored in alkaline pHs. The electrons can be produced by an anodic corrosion reaction at a different location on the metal object, and then travel through the metal, a conductor, to the cathodic reaction location. Thus, for example, the anodic corrosion reaction can be on a shaft of a bolt, and the cathodic reaction and detection of the corrosion can be on the head of the bolt.

In a specific embodiment, the anodic corrosion reaction can be on the non-visible surface of a second metal object in contact with a first metal object, and the cathodic reaction and detection of corrosion can be on the visible surface of the first metal object.

An experiment was designed to test the effectiveness of the encapsulated indicator to detect hidden corrosion when incorporated into a coating system. Several coating systems, as shown in Table 10, were prepared to find a coating system that would indicate crevice corrosion as can be expected to occur in a nut and bolt setup designed to duplicate the use of bolts to hold a structure. The epoxy/urethane coating system showed the ability of the coating to indicate hidden corrosion as evidenced by the appearance of a purple color (data not shown). This was observed even in systems 5 and 6 (Table 10), where the indicator was only coated on the ends of the nut and bolt, distant from the primary site of corrosion (data not shown). In these examples, the cathodic site (where $O_2$ reduction happens and the pH increases) is at the head of the bolt, and the anodic site (where metal corrodes or rusts) is at the hidden area where the bolt locates.

TABLE 10

Coating systems used for hidden corrosion indication testing.

| System number | Metal Substrate | Coating systems |
|---|---|---|
| 1 | Zinc galvanized nut and bolt | Clear urethane coating containing 10% phph microparticles. |
| 2 | Zinc galvanized nut and bolt | First coated with epoxy, then top coated with clear urethane containing 10% phph microparticles. |
| 3 | Sand blasted nut and bolt. | The ends of the nut and bolt were coated with inorganic zinc coating; the entire nut and bolt was coated with urethane containing 10% phph microparticles. |
| 4 | Sand blasted nut and bolt | The ends of the nut and bolt were coated with inorganic zinc coating. The entire nut and bolt was coated with epoxy and then top coated with a clear urethane containing 10% phph microparticles. |
| 5 | Zinc galvanized nut and bolt | The ends of the nut and bolt were coated with urethane containing 10% phph microparticles. |
| 6 | Zinc galvanized nut and bolt. | The ends of the nut and bolt were coated with epoxy and then top coated with urethane containing 10% phph microparticles. | pH-sensitive microparticles containing corrosion indicators were synthesized through interfacial polymerization reactions in an emulsion. pH-sensitive microparticles with corrosion indicator have also been developed using a modified in-situ polymerization process as well as a spray drying process. The microparticles are designed specifically to detect the pH changes that are associated with the onset of corrosion and respond autonomously to indicate its presence early.

A prototype smart coating for the autonomous detection of corrosion was prepared by blending pH-sensitive microparticles into commercially available coatings. Preliminary results showed that pH-sensitive microparticles can be used to detect corrosion before visible rust appears and also to detect corrosion in hidden areas.

EXAMPLE 6 pH-Sensitive Microparticle With Corrosion Inhibitors

During the microcapsule formulation development process, it became apparent that a microparticle with active components encapsulated throughout the whole matrix of the particle can be more advantageous for smart coatings for corrosion applications, especially for the indication and inhibition functions.

The inhibitor microparticle was conceived as a good alternative to microcapsules for delivery and release of an inhibitor for corrosion control in a coating. In the microparticle, the inhibitor could be interspersed throughout the polymer instead of just encased in a polymer wall. This would allow for a more controlled release of the inhibitor over time rather than all at once as occurs with a wall breakdown mechanism of a microcapsule.

Synthesis of the microparticle uses the water soluble prepolymer developed for the water-core microcapsules but in a more simplified process of formation. The synthesis process includes dissolving the inhibitor into a water-miscible solvent first, such as ethanol or isopropanol. The inhibitor solution is then added to a continuous water phase. This process allows the inhibitor to be incorporated into the particle rather than being dissolved into the water. While the process is not completely understood, we think that through a somewhat spontaneous microemulsion process (similar to the Ouzo Effect but less stable) the inhibitor solution is dispersed into droplets. The polymerization reaction then occurs at the interfaces of these droplets which causes the inhibitor to be incorporated into particles before being dissolved into the water. Two surfactants, SDS and gum arabic, and mixing techniques are used to control size and maintain particle distribution. Acid catalyst may or may not be used to speed up the polymerization reaction depending on the prepolymer and inhibitor used to form the microparticle.

Acidic Inhibitor Microparticles

The first inhibitor microparticle successfully synthesized was one using an inhibitor that was acidic in nature. These microparticle formulations are interesting because no additional acid is needed to catalyze the polymerization reaction that forms the particle. The acid inhibitor is what catalyzes the reaction and therefore serves a sort of dual purpose as a catalyst as well as an inhibitor.

Figure 16:
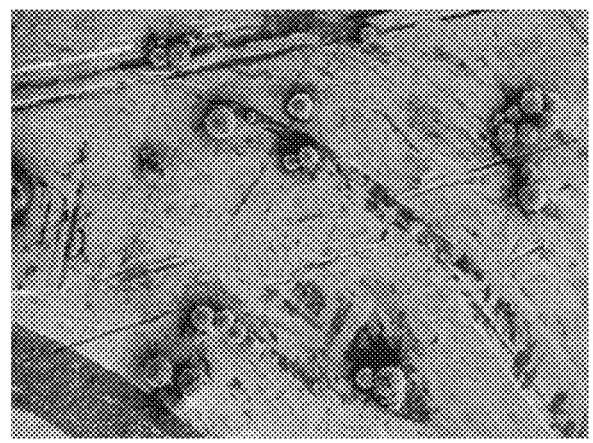
FIG. 16 is a SEM image of phenylphosphonic acid (PPA)-containing corrosion inhibitor microparticles, as described in Example 6.
Figure 16:
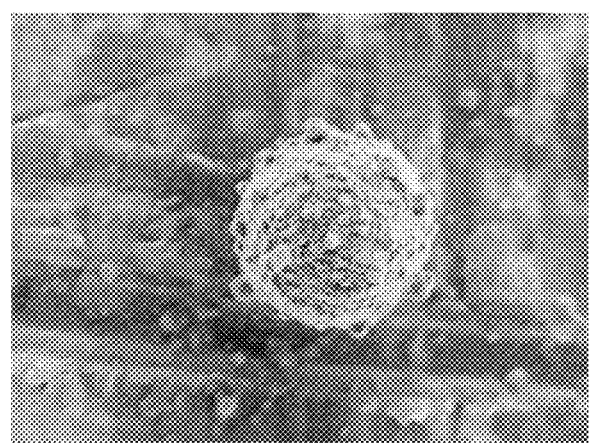

PPA was chosen as the first acid inhibitor for testing the microparticle process. The test results confirmed that it is an effective corrosion inhibitor for a steel substrate. PPA is an acid that can be used as an acid catalyst for the polymerization of the prepolymer for particle formation. The SEM images of the final product after spray drying are shown in FIG. 16.

Figure 17:
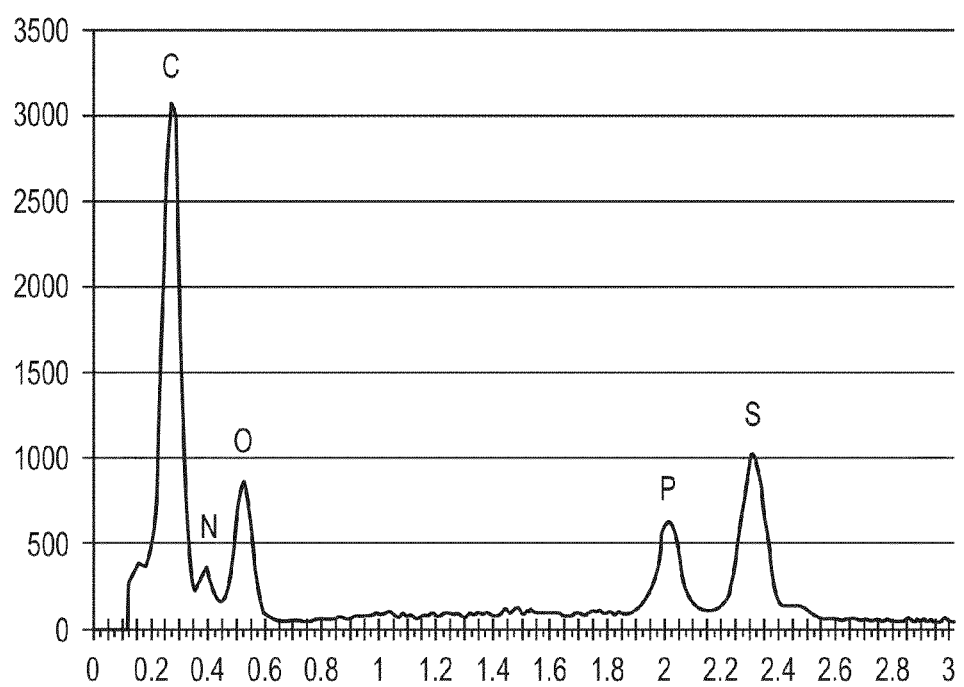
FIG. 17 shows the results of energy-dispersive X-ray spectroscopy (EDS) elemental analysis of the PPA-containing corrosion inhibitor microparticles, as described in Example 6.

FIG. 17 shows an elemental analysis obtained using energy-dispersive X-ray spectroscopy (EDS). The elements from the polymer: carbon (C), nitrogen (N), oxygen (O), and sulfur (S), as well as the phosphorus (P) from the inhibitor are found within the particle. Its presence in the particles proves that the PPA inhibitor was successfully incorporated in the MFPTT particles.

Figure 18:
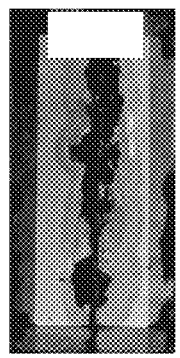
FIG. 18 shows salt fog testing results (1,000 hours) of the PPA microparticles in epoxy coating (bottom) versus controls (top). Panels A-C are untreated controls. Panel D was coated with PPA microparticles made with sodium dodecyl sulfate (SDS). Panels E and F were coated with PPA microparticles made without SDS.
Figure 18:
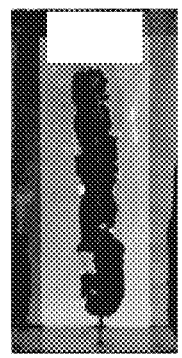
Figure 18:
Figure 18:
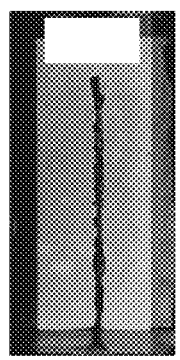
Figure 18:
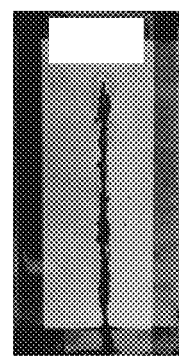
Figure 18:
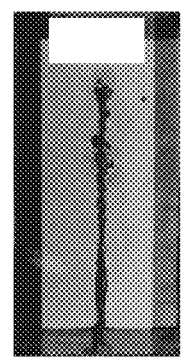

PPA particles were incorporated into an epoxy coating for testing. FIG. 18 shows that after 1,000 hours of salt fog testing, the coating with PPA particles provides much better corrosion protection than the control, especially in preventing corrosion under paint around scribes. Panels A-C are control coatings without PPA particles. Panel D coating contains PPA particles made with SDS. Panels E and F coatings contain PPA particles made without SDS.

Non-Acidic Inhibitor Microparticles

Another inhibitor microparticle was synthesized successfully using an inhibitor that was non-acidic in nature. These microparticle formulations require a certain water-miscible solvent, such as N-methylpyrrolidone (NMP) or dimethylformamide (DMF), to form the microparticle. These solvents are good solvents for the inhibitors, i.e. they can dissolve high amounts of the inhibitor, leading to a fairly large concentration of inhibitor in the microparticle, but they also seem to help promote the polymerization reaction as a catalyst would. These solvents actually accelerate the reaction by participating in it. The acid catalyst is still required to fully complete the polymerization reaction.

The inhibitors were dissolved into their respective solvents at fairly high concentrations leading to a high concentration of inhibitor (approximately 30%) incorporated into the microparticle.

pH-sensitive microparticles containing corrosion inhibitors were synthesized through interfacial polymerization reactions in an emulsion. Both acidic and non-acidic compounds can be incorporated into pH-sensitive microparticles if they can be dissolved into certain water-miscible solvents, such as THF, DMF, and NMP. Some of the inhibitor microparticles with high inhibitor concentration were incorporated into commercial coating systems and tested for their function. The preliminary results showed that these microparticles can be used as a corrosion inhibitor pigment in coatings.

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of forming microparticles comprising:
   dissolving or dispersing a prepolymer in a solvent A;
   mixing an active agent or active agents dispersed or dissolved in a solvent B with the prepolymer in solution or dispersion in solvent A; and
   polycondensing the prepolymer to form a polymer matrix and to form microparticles comprising the active agent or active agents dispersed in the polymer matrix;
   wherein the polymer backbone or a cross-linking segment of the polymer matrix is susceptible to hydrolysis in base;
   wherein solvents A and B are the same or different solvents;
   wherein solvents A and B are miscible with each other.

2. The method of claim 1 wherein solvents A and B are water-miscible solvents or solvent mixtures.

3. The method of claim 2 wherein the active agent or active agents are more soluble in water-miscible solvent B than in water.

4. The method of claim 1 wherein solvents A and B are non-water miscible solvents or solvent mixtures.

5. The method of claim 1 wherein the active agent or active agents are one or more corrosion indicators or corrosion inhibitors.

6. The method of claim 5 wherein the corrosion indicator comprises phenolphthalein; fluorescein; FERROZINE; tiron; 1,10-phenanthroline; or 8-hydroxyquinoline-5-sulfonic acid.

7. The method of claim 5 wherein the corrosion inhibitor comprises phenylphosphonic acid; molybdate; nitrite; nitrate; phosphate; borate; silicate; vanadate; cerium salt; sodium tannte; otassium oxalate; benzotriazole; thiourea bezotriazole; 2-mercaptobenzothiazole; 2-mercaptobenzimidazole; 2-(benzothiazol-2-ylsulfanyl)-succinic acid; 3,5 diaminobenzoic acid; quinaldic acid; sarcosine; 8-hydroxyquinoline; salicylaldoxime; or film-forming polyamine.

8. The method of claim 1 wherein at least 10% by weight of the microparticles is the active agent or active agents.

9. The method of claim 1 wherein the polymer backbone or a cross-linking segment of the polymer matrix comprises ester, thioester, anhydride, amide, or ortho ester linkages.

10. The method of claim 1 wherein the prepolymer is formed in solvent A from a mixture of reactants.

11. The method of claim 10 wherein the prepolymer reactants comprise a compound having at least three arms that contain ester, thioester, or anhydride bonds.

12. The method of claim 10 wherein the prepolymer reactants comprise melamine and formaldehyde.

13. The method of claim 10 wherein the prepolymer reactants comprise pentaerythritol tetra(3-mercaptopropionate).

14. The method of claim 10 wherein the prepolymer reactants comprise a compound with a plurality of mercapto groups.

15. The method of claim 10 wherein the prepolymer reactants comprise a compound with a plurality of ester, thioester, or anhydride bonds.

16. The method of claim 10 wherein the prepolymer is formed in aqueous solution with one or more surfactants.

17. The method of claim 1 wherein most of the microparticles have a diameter below 25 microns.

18. A composition comprising microparticles, the microparticles comprising:
    a polymer matrix and an active agent or active agents dispersed in the polymer matrix;
    wherein the active agent or active agents are one or more corrrosion indicators or corrosion inhibitors;
    wherein the polymer backbone or a cross-linking segment of the polymer matrix is susceptible to hydrolysis in base.

19. The composition of claim 18 wherein the microparticles do not have a hollow interior free of the polymer.

20. The composition of claim 18 wherein the composition, when coated on a metal fastener head, is able to produce a visible colored or fluorescent indication on the metal fastener head of corrosion on the metal fastener shaft.

21. The composition of claim 18 wherein the composition, when coated on the surface of a first metal object in contact with a second metal object, is able to produce a visible colored or fluorescent indication on the surface of first metal object of corrosion on the non-visible surface of first metal object or on non-visible second metal object.

22. The composition of claim 18 wherein the polymer comprises melamine residues.

23. The composition of claim 18 wherein the polymer comprises residues of a monomer with at least three arms that contain ester, thioester, or anhydride bonds.

24. The composition of claim 18 wherein most of the microparticles have a diameter below 25 microns.

25. The composition of claim 18 wherein the microparticles are formed by a process comprising:
  dissolving or dispersing a prepolymer in a solvent A;
  mixing an active agent or active agents dispersed or dissolved in a solvent B with the prepolymer in solution or dispersion in solvent A; and
  polycondensing the prepolymer to form a polymer matrix and to form microparticles comprising the active agent or active agents dispersed in the polymer matrix;
  wherein the polymer backbone or a cross-linking segment of the polymer matrix is susceptible to hydrolysis in base;
  wherein solvents A and B are the same or different solvents;
  wherein solvents A and B are miscible with each other.

26. The composition of claim 18 wherein the composition further comprises polyurethane.

27. The composition of claim 18 wherein the composition is a latex composition.

28. The composition of claim 18 wherein the composition further comprises epoxy.

29. The composition of claim 18 wherein the composition is a coating on a metal object.

30. A metal object partially or fully coated with a composition according to claim 18.

31. A method of detecting corrosion comprising:
  (a) obtaining a metal object partially or fully coated with a coating composition comprising microparticles, the microparticles comprising:
    a polymer matrix and an active agent or active agents dispersed in the polymer matrix;
    wherein the active agent or active agents are one or more corrosion indicators;
    wherein the polymer backbone or a cross-linking segment of the polymer matrix is susceptible to hydrolysis in base; and
  (b) monitoring the object for visible changes of color or fluorescence from the one or more corrosion indicators that would indicate corrosion.

32. The method of claim 31 wherein the metal object is a first metal object in contact with a second metal object, wherein the coating composition is on the surface of the first metal object;
  wherein the method comprises monitoring the first metal object for visible changes on the surface that indicates corrosion on the non-visible surface of the first metal object or the non-visible second metal object.

33. The method of claim 31 wherein the metal object is a screw, bolt, nut, rivet, or any other metal fastening device.

34. The method of claim 31 wherein the metal object is a screw, bolt, rivet, or metal fastener having a shaft and a head, wherein the coating composition is on the head of the screw, bolt, rivet, or metal fastener;
  wherein the method comprises monitoring the screw, bolt, rivet, or metal fastener for visible changes on the head that indicate corrosion on the shaft.

35. A composition comprising microparticles, the microparticles comprising:
  a polymer matrix and an active agent or active agents dispersed in the polymer matrix;
  wherein the polymer backbone or a cross-linking segment of the polymer matrix is susceptible to hydrolysis in base;
  wherein the polymer backbone or a cross-linking segment of the polymer matrix comprises residues of a monomer having at least three arms that contain ester, thioester, or anhydride bonds.

* * * * *